United States Patent
Snape et al.

(10) Patent No.: US 6,828,318 B2
(45) Date of Patent: Dec. 7, 2004

(54) 2-ADAMANTYLETHYLAMINES AND THEIR USE IN THE TREATMENT OF CONDITIONS GENERALLY ASSOCIATED WITH ABNORMALITIES IN GLUTAMATERGIC TRANSMISSION

(75) Inventors: Michael Frederick Snape, Winnersh (GB); Roger John Gillespie, Winnersh (GB); Claire Elizabeth Dawson, Winnersh (GB); Steven Michael McAteer, Winnersh (GB); Suneel Gaur, Winnersh (GB)

(73) Assignee: Vernalis Research Limited, Winnersh (GB)

( * ) Notice: Subject to any disclaimer, the term of this patent is extended or adjusted under 35 U.S.C. 154(b) by 42 days.

(21) Appl. No.: 10/333,952
(22) PCT Filed: Jul. 25, 2001
(86) PCT No.: PCT/GB01/03321
§ 371 (c)(1), (2), (4) Date: Mar. 31, 2003
(87) PCT Pub. No.: WO02/08219
PCT Pub. Date: Jan. 31, 2002

(65) Prior Publication Data
US 2003/0207881 A1 Nov. 6, 2003

(30) Foreign Application Priority Data
Jul. 25, 2000 (GB) .............................. 0018272

(51) Int. Cl.[7] .................. C07D 333/06; A61K 31/381; A61K 31/5377; A61K 31/4025; A61K 31/4436
(52) U.S. Cl. .................. 514/231.5; 514/326; 514/422; 514/438; 514/650; 514/654; 514/659; 514/146; 546/212; 546/213; 548/527; 549/74; 564/338; 564/374; 564/454
(58) Field of Search ................. 514/231.5, 326, 514/422, 438, 650, 654, 659; 544/146; 546/212, 213; 548/527; 549/74; 564/338, 374, 454

(56) References Cited

FOREIGN PATENT DOCUMENTS

| GB | 1 264 500 A | 2/1972 |
|---|---|---|
| WO | WO 97/23202 A | 7/1997 |
| WO | WO 99/31075 A | 6/1999 |
| WO | WO 99/38841 A | 8/1999 |
| WO | WO 00/44371 A | 8/2000 |

OTHER PUBLICATIONS

Van Hes et al., "Synthesis and Antiviral Activities of Adamanatane Spiro Compounds," *Journal of Medicinal Chemistry* (1972), vol. 15, No. 2, pp. 132–136.

Primary Examiner—Brian Davis
(74) Attorney, Agent, or Firm—Foley & Lardner LLP

(57) ABSTRACT

Compounds of formula (1):

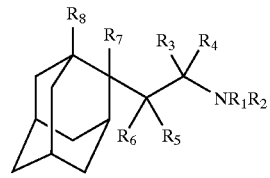

(1)

wherein $R_1, R_2, R_3, R_4, R_5$ and $R_6$ are independently selected from hydrogen, alkyl, aryl and non-aromatic heterocyclic groups, or each of one or more pair(s) of the substituent groups $R_1$ to $R_6$ may together form a 3,4,5,6,7 or 8-membered ring containing 0,1 or 2 heteroatom(s);

$R_7$ is selected from alkyl, aryl and non-aromatic heterocyclic groups; and $R_8$ is selected from hydrogen, halogen, alkyl, aryl and non-aromatic heterocyclic groups;

and pharmaceutically acceptable salts and prodrugs thereof, are useful for treating conditions generally associated with abnormalities in glutamatergic transmission.

34 Claims, 5 Drawing Sheets

2-ADAMANTYLETHYLAMINES AND THEIR USE IN THE TREATMENT OF CONDITIONS GENERALLY ASSOCIATED WITH ABNORMALITIES IN GLUTAMATERGIC TRANSMISSION

This application is a 371 of PCT/GB01/03321 filed Jul. 25, 2001.

BACKGROUND OF THE INVENTION

The present invention relates to 2-adamantylethylamines and their use in the treatment of conditions generally associated with abnormalities in glutamatergic transmission.

The excitatory neurotransmission underlying brain function is primarily (about 80 percent) dependent on the action of glutamate and other related neurotransmitters on specific receptors activated by the excitatory amino acids. These receptors fall into several categories, one of which is the glutamate receptor specifically sensitive to the agonist N-methyl-D-aspartate (the NMDA receptor). NMDA receptor subtypes are ubiquitously expressed in mammalian brain and have unique properties underlying their role in synaptic function and plasticity. In view of the central role of these receptors in normal central nervous system function, numerous suggestions have been made as to the utility of drugs acting at this receptor to modulate the processes underlying various disease states. The NMDA receptor has been studied with particular interest in relation to its apparent involvement in the pathophysiology of neurodegenerative diseases and states of neuropathic pain.

Non-competitive antagonists at this receptor should be particularly advantageous in the treatment of diseases since such compounds would have activity that should not be overcome by high levels of endogenous agonists and would act equally well independent of the endogenous agonist activating the receptor. This is important since high levels of endogenous glutamate can occur in certain pathological processes and there are a variety of different endogenous agonists that can act through a variety of specific modulatory agonist binding sites on the receptor.

A number of NMDA antagonists have been disclosed which operate by binding to the ion-channel of the NMDA receptor. The advantage of channel blockers is that they operate only on the "open" channel and therefore do not affect unactivated receptors. In addition they are effective regardless of the mechanism of receptor stimulation and their effect will not be diminished by large concentrations of endogenous agonist.

Given that the NMDA receptor plays a primary role in normal central nervous system function, it is not surprising that certain drugs acting to block or antagonise the function of this receptor affect normal function within the brain. This may be manifested as central nervous system side effects such as hallucinations, confusion, paranoia, aggression, agitation and catatonia. These side effects can be described as a psychotic state and the drugs that induce them are known as psychotomimetic NMDA antagonists. Such side effects limit the utility of these compounds in treating disease states. NMDA receptor antagonists that have efficacy in treating central nervous system disorders but without such psychotomimetic side effects would have a clear therapeutic advantage. Thus, in view of the crucial role played by the NMDA receptor in either the progression or expression of the disease pathology and process, it is an object of this invention to provide compounds for the treatment of central nervous system disorders which modulate the activity of the NMDA receptor but which are well-tolerated in the sense of having a markedly reduced propensity to induce psychotomimetic side effects.

The present invention is particularly concerned with the treatment of neurodegenerative disorders and the treatment of pain. There is a large body of evidence to suggest that either an excitotoxic or slow excitotoxic pathological over-activation of the NMDA receptor induces the death of neurons in a variety of disorders such as ischaemic stroke, other forms of hypoxic injury, haemorrhagic brain injury, traumatic brain injury, Alzheimer's disease, Parkinson's disease, Huntington's disease and other dementing diseases. There is thus clear evidence that antagonism of the NMDA receptor will reduce or prevent the neurodegeneration that underlies the disease process in these and related conditions. There is also evidence to suggest that a well-tolerated compound will allow effective symptomatic treatment of the manifestations of the disease process in these disorders as well as reducing the primary underlying neurodegeneration process. Also, it is known that some disorders previously described as involving acute neurodegeneration have longer than expected elevations in extracellular concentrations of glutamate and consequently require longer than expected treatment with NMDA antagonists. There would therefore be a therapeutic advantage for new drugs which are well-tolerated and which can therefore be administered chronically.

Similarly, there is a substantial body of evidence available in the literature, regarding both pre-clinical and clinical studies, suggesting NMDA receptor involvement in the perception of pain, the generation of persistent neuropathic pain states, and the development of tolerance to traditional analgesics. It has been long known that NMDA receptor antagonists prevent behaviours mediated by nociceptive stimuli in experimental animals, as would be expected of analgesics. Similarly, experimental studies on C-fibre responses, for example, have shown the role of NMDA receptor antagonists in blocking long lasting activity thought to reflect neuropathic pain. Neuropathic pain is not well treated by traditional analgesics, such as opiates or non-steroidal anti-inflammatory agents. Neuropathic pain occurs during diabetic neuropathy, AIDS-related neuropathy, postherpetic neuralgia, chronic degenerative spinal disease, sympathetic dystrophies, post-amputation stump pain (phantom limb), trigeminal neuralgia, thalamic pain syndrome, sciatica and multiple sclerosis.

Whilst pain due to cancer can be treated with opiate analgesics, the effect of opiates in producing pain relief in cancer diminishes with time. This phenomenon is known as opiate tolerance. Both pre-clinical and clinical studies have shown that NMDA antagonists prevent the development of opiate tolerance and have an "opiate sparing" effect. This means that administration of an NMDA antagonist alongside an opiate may result in the treatment of cancer pain using less opiate and with a more persistent effect.

The published literature contains references to a number of compounds and classes of compounds purported to be useful as NMDA antagonists.

The compounds Amantadine and Memantine and related anti-viral agents have been known for many years.

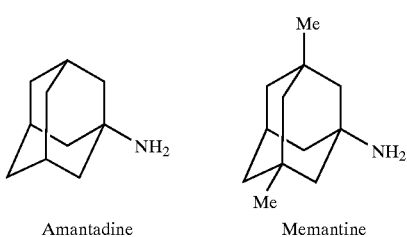

Amantadine   Memantine

Patent applications have been filed directed to the use of Memantine in the treatment of Parkinson's Disease in the 1970s and as an NMDA antagonist in 1990 (see EP-A-0392059 and U.S. Pat. No. 5,061,703). Furthermore, International Patent application WO94/05275 proposes the use of Amantadine and related compounds such as Memantine in the treatment and prevention of non-ischaeric, long term NMDA receptor-mediated neuronal degeneration. An increase in affinity for the NMDA receptor due to substitution of the adamantane ring of Amantadine with alkyl groups was noted and published in Kornhuber et al. (Eur. J. Pharmacol., 1991, 206, 297–300). Structure-activity relationships relating to 1-(adamantyl)alkanamines are reported by Kroemer et al. (J. Med. Chem.,1998, 41, 393–400), by Parsons et al. (Neuropharmacology, 1995, 34, 1239–1258) and by Fytas et al. (II Farmaco,1994, 49, 641–647).

As discussed above, psychotomimetic side-effects are observed during the use of a number of well known NMDA receptor channel blockers and therefore it will be a considerable advantage to identify clinically well-tolerated antagonists where such side effects are minimised.

The use of a number of the known NMDA antagonists such as Dizocilpine (MK-801), phencyclidine (PCP), Cerestat and Ketamine gives rise to a number of side effects which render these compounds unsuitable for use in treatment. In particular, administration of the compounds is associated with perceptual and cognitive disturbances of a kind that resemble naturally-occurring psychotic states.

In addition, the perceptual and cognitive side effects of the compounds become more pronounced after the onset of puberty and sexual maturation, and these compounds are therefore particularly unsuitable for the treatment of adults. This developmental change has been demonstrated empirically in both experimental animals and in man, and is paralleled in experimental animals by brain hypermetabolism.

As noted above, non-competitive NMDA receptor channel blockers are frequently associated with the causation of psychotic states in clinical use. The prototypical compound phencyclidine (PCP), when administered to man, usually achieves tissue levels similar to the potency of this compound in its action as an NMDA receptor channel blocker. Such tissue levels are associated with an acute psychotic state clinically indistinguishable from an acute schizophreniform breakdown. In experimental animals administration of doses that produce equivalent tissue levels induces a characteristic behavioural state. This behavioural state comprises of the production of head weaving, circling, reciprocal fore paw treading and hyperactivity, as is known as the "PCP syndrome". The induction of the "PCP syndrome" is unique and specific to NMDA receptor channel blocking agents that are psychotomimetic in man. Competitive antagonists acting at agonist binding sites on the NMDA receptor do not elicit this "PCP syndrome" and are not psychotomimetic in man. Our data show that memantine, an NMDA receptor channel blocking agent, also elicits "PCP syndrome", as shown in FIG. 1.

We have also shown that ketamine, an NMDA receptor channel blocking agent with a similar binding potency to memantine, also produces "PCP syndrome" confirming that this syndrome reflects activity in a compound known to be psychotomimetic in man (see FIG. 3).

In summary, there is a need for an NMDA antagonist which is well-tolerated and does not give rise to the side effects associated with previous clinically investigated NMDA antagonists.

DETAILED DESCRIPTION OF THE INVENTION

Figure 1:
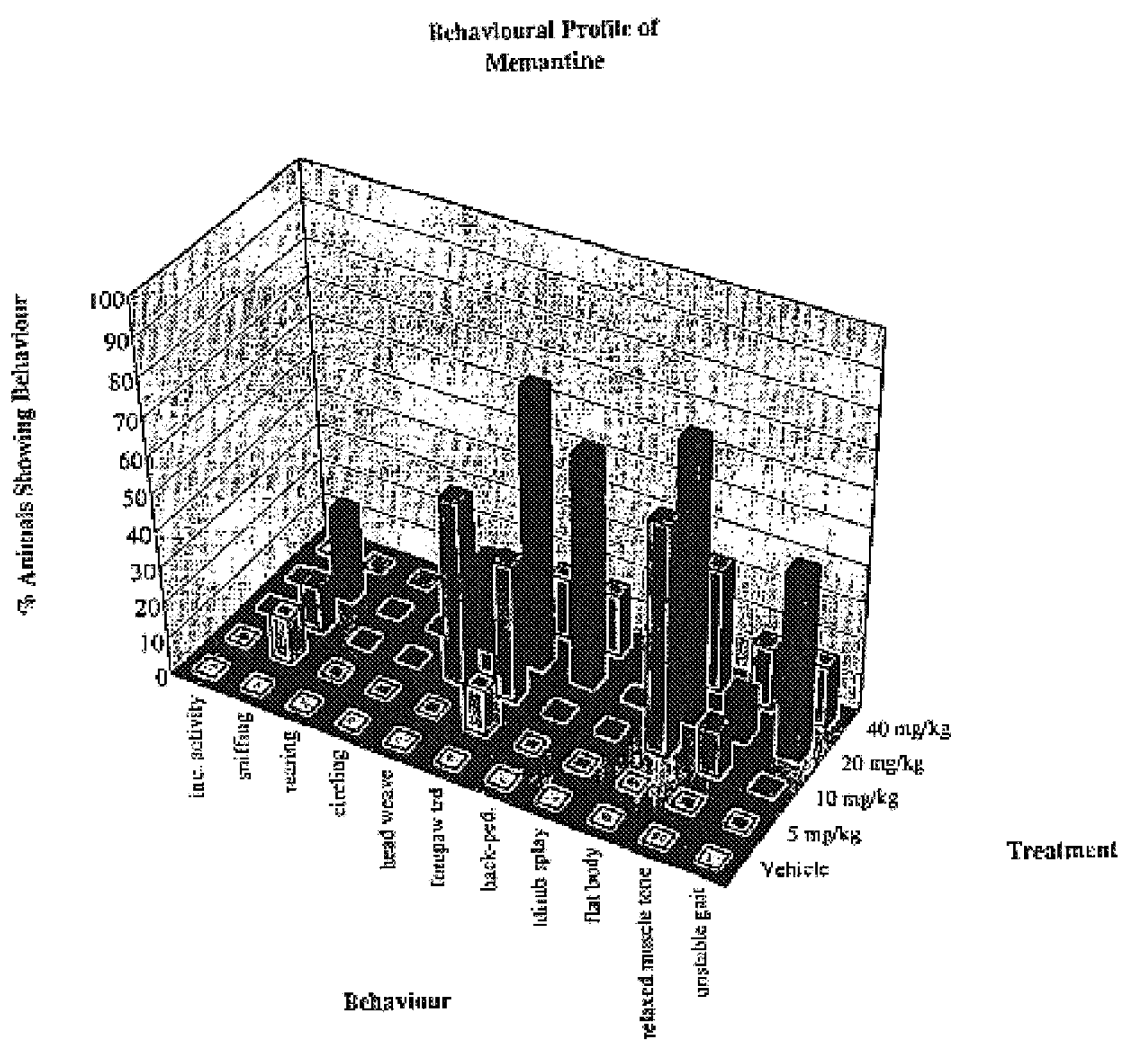
FIG. 1 shows the behavioral profile of memantine. Memantine was administered intraperitoneally at doses of 5, 10, 20 and 40 mg/kg twenty minutes prior to testing, and the percentage of animals in groups of n=8 animals showing PCP related behaviors was scored.

A number of compounds have now been found that show affinity for the NMDA receptor and are useful in the treatment of conditions generally associated with abnormalities in glutamatergic transmission such as stroke, traumatic brain injury and neurodegenerative diseases such as Parkinson's and Alzheimer's disease, as well as pain states. It has also been found that the compounds have a surprisingly favourable behavioural profile, being apparently devoid of the pre-clinical side effect liability associated with non-competitive blockers of the NMDA receptor channel.

According to the present invention there is provided the use of a compound of formula (1):

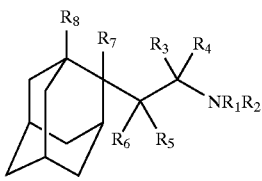

(1)

wherein $R_1$, $R_2$, $R_3$, $R_4$, $R_5$ and $R_6$ are independently selected from hydrogen, alkyl, aryl and non-aromatic heterocyclic groups, or each of one or more pair(s) of the substituent groups $R_1$ to $R_6$ may together form a 3, 4, 5, 6, 7 or 8-membered ring containing 0, 1 or 2 heteroatom(s);

$R_7$ is selected from alkyl, aryl and non-aromatic heterocyclic groups; and $R_8$ is selected from hydrogen, halogen, alkyl, aryl and non-aromatic heterocyclic groups;

and pharmaceutically acceptable salts and prodrugs thereof, in the manufacture of a medicament for use in the treatment of a condition generally associated with abnormalities in glutamatergic transmission.

The compounds of the present invention are active as NMDA antagonists and are well-tolerated in that side effects are minimised.

As used herein, the term "alkyl" means a branched or unbranched, cyclic or acyclic, saturated or unsaturated (e.g. alkenyl or alkynyl) hydrocarbyl radical. Where cyclic, the alkyl group is preferably $C_3$ to $C_{12}$, more preferably $C_3$ to $C_7$, more preferably $C_5$ to $C_7$. Where acyclic, the alkyl group is preferably $C_1$ to $C_{10}$, more preferably $C_1$ to $C_6$, more preferably methyl, ethyl, propyl (n-propyl or isopropyl), butyl (n-butyl, isobutyl, tertiary-butyl or sec-butyl) or pentyl (including n-pentyl and iso-pentyl), more preferably methyl. It will be appreciated therefore that the term "alkyl" as used herein includes alkyl (branched or unbranched), alkenyl (branched or unbranched), alkynyl (branched or unbranched), cycloalkyl, cycloalkenyl and cycloalkynyl.

As used herein, the term "lower alkyl" means a branched or unbranched, cyclic or acyclic, saturated or unsaturated (e.g. alkenyl or alkynyl) hydrocarbyl radical, wherein a cyclic lower alkyl group is $C_5$, $C_6$ or $C_7$, and wherein an acyclic lower alkyl group is methyl, ethyl, propyl (n-propyl or isopropyl) or butyl (n-butyl, isobutyl, tertiary-butyl or sec-butyl), more preferably methyl.

As used herein, the term "aryl" means a carbocyclic aromatic group, such as phenyl or naphthyl, or a heteroaromatic group containing one or more, and preferably one, heteroatom(s) such as pyridyl, pyrrolyl, furyl, thienyl, thiazolyl, isothiazolyl, oxazolyl, isoxazolyl, oxadiazolyl, thiadiazolyl, pyrazolyl, imidazolyl, triazolyl, tetrazolyl, pyrimidinyl, pyridazinyl, pyrazinyl, triazinyl, indolyl, indazolyl, quinolinyl, quinazolinyl, benzimidazolyl, benzothiazolyl, benzoxazolyl, benzisoxazolyl and benzisothiazolyl. Preferably, the aryl group comprises phenyl or thienyl, more preferably phenyl.

As used herein, the term "carbocyclic group" refers to a ring wherein all the ring atoms are carbon atoms.

As used herein, the term "non-aromatic heterocyclic group" refers to a ring or ring system which contains one or more heteroatom(s) (preferably heteroatoms(s) selected from N, O and S) and which is either saturated or partially unsaturated, such as piperidine, piperazine, morpholine, aziridine, azetidine, pyrrolidine, pyrroline or tetrahydrofuran.

As used herein, the term "partially unsaturated" refers to a ring which contains unsaturated ring atoms but which is not aromatic. In a preferred embodiment, the term "partially unsaturated" refers to a ring which contains one or two double bonds.

As used herein, the term "alkoxy" means alkyl-O—. As used herein, the term "aryloxy" means aryl-O—.

As used herein, the term "halogen" means a fluorine, chlorine, bromine or iodine radical, preferably a fluorine, chlorine or bromine radical.

As used herein, the term "pharmaceutically acceptable salt" means any pharmaceutically acceptable salt of the compound of formula (I). Salts may be prepared from pharmaceutically acceptable non-toxic acids and bases including inorganic and organic acids and bases. Such acids include acetic, benzenesulfonic, benzoic, camphorsulfonic, citric, dichloroacetic, ethanesulfonic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Particularly preferred are fumaric, hydrochloric, hydrobromic, phosphoric, succinic, sulfuric and methanesulfonic acids, and particularly hydrochloric acid. Acceptable base salts include alkali metal (e.g. sodium, potassium), alkaline earth metal (e.g. calcium, magnesium) and aluminium salts.

As used herein the term "prodrug" means any pharmaceutically acceptable compound which undergoes biotransformation to a compound of formula (1) prior to exhibiting it's pharmacological effects. The use of prodrugs is widely described in the literature and the term "prodrug" has been defined by many authors for example in Burger's Medicinal Chemistry and Drug Design, $5^{th}$ Edition, 1995, Ed. M. E. Wolff, Vol 1, Principles and Practice, Pages 172 and 950. Many molecules which possess the optimal structural configuration and physicochemical properties for eliciting the desired pharmacological action and therapeutic effect do not possess the best molecular form and properties for delivery to the desired site of action. By attaching a "pro-moiety" to the "active moiety" a prodrug is formed that is designed to overcome the barrier which hinders the optimal use of the active principle. Usually the prodrug contains a covalent link between the "active moiety" and the "carrier moiety" which cleaves by biotransformation to release the "active moiety" after being absorbed into the body. Chemical modification of drugs into prodrugs can often improve the physicochemical properties such as water-solubility and lipophilicity and transport of the drug to its site of action leading to improved bioavailability. The use of prodrugs for amines is well known and has been reviewed in the literature for example by Pitman (Med. Res. Rev., 1981, 1, 189–214). Examples of compounds which may be useful as prodrugs of amines of formula $R_1R_2NH$ include amides ($R_1R_2NCOR_3$), alkyl carbamates ($R_1R_2NCO_2R_3$), N-(acyloxy)alkyl carbamates ($R_1R_2NCO_2CH(R_3)OCOR_4$), (phosphoryloxy) methyl carbamates ($R_1R_2NCO_2CH_2OPO_3H_2$), N-(acyloxy) methyl derivatives ($R_1R_2NCH(R_3)OCOR_4$), N-Mannich bases ($R_1R_2NCH_2NR_3R_4$), and for primary amines of formula $R_1NH_2$, N-(N,N-dialkylamino)methylene derivatives ($R_1R_2N=CHNR_2R_3$).

In one embodiment, the term "treatment" includes prophylactic treatment. In a preferred embodiment, the term "treatment" includes the reduction or prevention of the progression of the condition to be treated, particularly where this condition is a neurodegenerative disease.

Where any of $R_1$ to $R_8$ is an alkyl group as defined in formula (I) above, then that alkyl group may be substituted or unsubstituted. Where any of $R_1$ to $R_8$ is an aryl group as defined in formula (I), then said aryl group may be substituted or unsubstituted. Where any pair of $R_1$ to $R_6$ together form a ring, said ring may be substituted or unsubstituted. Where any of $R_1$ to $R_8$ or any ring-forming pair of $R_1$ to $R_6$ is substituted, there will generally be 1 to 3 substituents present, preferably 1 substituent. Substituents may include:

carbon-containing groups such as alkyl, aryl, (e.g. substituted and unsubstituted phenyl), arylalkyl; (e.g. substituted and unsubstituted benzyl);

halogen atoms and halogen containing groups such as haloalkyl (e.g. trifluoromethyl), haloaryl (e.g. chlorophenyl);

oxygen containing groups such as alcohols (e.g. hydroxy, hydroxyalkyl, hydroxyaryl, (aryl)(hydroxy)alkyl), ethers (e.g. alkoxy, aryloxy, alkoxyalkyl, aryloxyalkyl, alkoxyaryl, aryloxyaryl), aldehydes (e.g. carboxaldehyde), ketones (e.g. alkylcarbonyl, arylcarbonyl, alkylcarbonylalkyl, alkylcarbonylaryl, arylcarbonylalkyl, arylcarbonylaryl, arylalkylcarbonyl, arylalkylcarbonylalkyl, arylalkylcarbonylaryl)

acids (e.g. carboxy, carboxyalkyl, carboxyaryl), acid derivatives such as esters (e.g. alkoxycarbonyl, aryloxycarbonyl, alkoxycarbonylalkyl, aryloxycarbonylalkyl, alkoxycarbonylaryl, aryloxycarbonylaryl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl or arylalkylaminocarbonyl, alkylcarbonylamino, arylcarbonylamino or arylalkylcarbonylamino), carbamates (eg. alkoxycarbonylamino, aryloxycarbonylamino, arylalkyloxycarbonylamino, aminocarbonyloxy, mono- or di-alkylaminocarbonyloxy, arylaminocarbonyloxy or arylalkylaminocarbonyloxy) and ureas (eg. mono- or di-alkylaminocarbonylamino, arylarninocarbonylamino or arylalkylaminocarbonylamino);

nitrogen containing groups such as amines (e.g. amino, mono- or dialkylamino, arylamino, aminoalkyl, mono- or dialkylaminoalkyl), azides, nitriles (e.g. cyano, cyanoalkyl), nitro;

sulfur containing groups such as thiols, thioethers, sulfoxides, and sulfones (e.g. alkylthio, alkylsulfinyl, alkylsulfonyl, alkylthioalkyl, alkylsulfinylalkyl, alkylsulfonylalkyl, arylthio, arylsulfinyl, arylsulfonyl, arylthioalkyl, arylsulfinylalkyl, arylsulfonylalkyl)

and heterocyclic groups containing one or more, preferably one, heteroatom, (e.g. thienyl, furanyl, pyrrolyl, imidazolyl, pyrazolyl, thiazolyl, isothiazolyl, oxazolyl, isoxazolyl, tetrazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

As used herein the term "conditions generally associated with abnormalities in glutamatergic transmission" refers particularly to conditions treatable by blockade of the N-methyl-D-aspartate (NMDA) receptor, i.e. conditions in which administration of an NMDA receptor antagonist would be beneficial, and primarily includes ischaemic stroke, haemorrhagic stroke, subarrachnoid haemorrhage, subdural haematoma, coronary artery bypass surgery, neurosurgery, traumatic brain injury, traumatic spinal injury, Alzheimer's disease, Parkinson's disease, Huntington's disease, Pick's disease, Lewy body disease, senile dementia, spongiform encephalopathies, prion-protein induced neurotoxicity, perinatal asphyxia, demyelinating disease, multiinfarct dementia, vascular dementia, dementia pugilans, drug dependence, alcohol withdrawal, opiate withdrawal, motor neurone disease, multiple sclerosis, acute and chronic pain including neuropathic pain, cancer pain, trigeminal neuralgia, migraine, pain caused by excessive vasodilation (including undesirable vasodilation in the cerebral vasculature (vasodilatory headache)), cluster headache, primary and secondary hyperalgesia, inflammatory pain, nociceptive pain, tabes dorsalis, phantom limb pain, spinal cord injury pain, central pain, post herpetic pain, HIV pain and diabetic neuropathy. In addition, the term also includes the following conditions: epilepsy, AIDS dementia, multiple system atrophy, progressive supra-nuclear palsy, Friedrich's ataxia, autism, fragile X syndrome, tuberous sclerosis, attention deficit disorder, olivio-ponto-cerebellar atrophy, cerebral palsy, drug-induced optic neuritis, peripheral neuropathy, myelopathy, ischaemic retinopathy, glaucoma, cardiac arrest, meningitis, encephalitis, depression, bi-polar disorder, schizophrenia, psychosis, behaviour disorders, impulse control disorders, pre-eclampsia, neuroleptic malignant syndrome, chronic fatigue syndrome, anorexia nervosa, anxiety disorders, generalised anxiety disorder, panic disorder, phobias, fresh water drowning and decompression.

In one embodiment of the invention, the compounds of formula (1) are selected from compounds wherein $R_1$, $R_2$, $R_3$, $R_4$, $R_5$ and $R_6$ are independently selected from hydrogen, alkyl and aryl, or each of one or more pair(s) of the substituent groups $R_1$ to $R_6$ may together form a 3, 4, 5, 6, 7 or 8-membered ring containing 0, 1 or 2 heteroatom(s);

$R_7$ is selected from alkyl and aryl; and $R_8$ is selected from hydrogen, halogen, alkyl and aryl.

In a further embodiment of the invention, the compounds of formula (1) are selected from compounds wherein $R_1$, $R_2$, $R_3$, $R_4$, $R_5$ and $R_6$ are independently selected from hydrogen, alkyl and aryl, or each of one or more pair(s) of the substituent groups $R_1$ to $R_6$ may together form a 3, 4, 5, 6, 7 or 8-membered ring containing 0, 1 or 2 heteroatom(s);

$R_7$ is selected from alkyl and aryl; and $R_8$ is selected from hydrogen, alkyl and aryl.

In the compound of formula (1), preferably $R_1$ to $R_6$ are independently selected from hydrogen and alkyl, and preferably hydrogen. Where any of $R_1$ to $R_6$ is selected from alkyl, it is preferred that said alkyl group is a lower alkyl group, and preferably an acyclic lower alkyl group, and preferably methyl.

Preferably at least one of $R_1$ and $R_2$ is hydrogen or methyl, preferably hydrogen, and preferably both $R_1$ and $R_2$ are hydrogen.

In the compound of formula (1), preferably one or both of $R_3$ and $R_4$ is/are hydrogen or methyl, preferably hydrogen, and more preferably both are hydrogen.

In the compound of formula (1), preferably one or both of $R_5$ and $R_6$ is/are hydrogen or methyl, preferably hydrogen, and more preferably both are hydrogen.

In one embodiment, $R_7$ is selected from cycloalkyl, unsubstituted acyclic alkyl (preferably lower alkyl), aryl-substituted acyclic alkyl (preferably lower alkyl) and aryl, and preferably from cycloalkyl and aryl, and more preferably from aryl. In an alternative embodiment, $R_7$ is selected from cycloalkyl, unsubstituted acyclic alkyl (preferably lower alkyl), acyclic alkyl (preferably lower alkyl) substituted by a non-aromatic heterocyclic group, acyclic alkyl (preferably lower alkyl) substituted by aryl, non-aromatic heterocyclic groups, and aryl; preferably from unsubstituted alkyl (preferably acyclic, preferably lower alkyl), alkyl (preferably acyclic, preferably lower alkyl) substituted by a non-aromatic heterocyclic group, alkyl (preferably acyclic, preferably lower alkyl) substituted by aryl, non-aromatic heterocyclic groups, and aryl; more preferably from unsubstituted alkyl (preferably acyclic, preferably lower alkyl), alkyl (preferably acyclic, preferably lower alkyl) substituted by a non-aromatic heterocyclic group, alkyl (preferably acyclic, preferably lower alkyl) substituted by aryl, and aryl; and more preferably from unsubstituted acyclic alkyl (preferably lower alkyl), alkyl (preferably acyclic, preferably lower alkyl) substituted by aryl, and aryl. Where $R_7$ is selected from aryl or aryl-substituted alkyl, reference to said aryl specifically includes reference to heteroaromatic groups. Where $R_7$ is aryl-substituted alkyl, said aryl is preferably a carbocyclic aromatic group.

In a preferred embodiment, $R_7$ is selected from monocyclic substituted or unsubstituted, preferably unsubstituted, aryl (including heteroaromatic groups).

In a particularly preferred embodiment, $R_7$ is a substituted or unsubstituted carbocyclic aromatic group, preferably unsubstituted, preferably phenyl.

Where $R_7$ is an heteroaromatic group, it is preferred that $R_7$ contains only one heteroatom. In one embodiment, $R_7$ is thienyl, thiazolyl, pyridyl or furyl, preferably thienyl, preferably 2-thienyl.

Where $R_7$ is substituted aryl, particularly substituted phenyl, there is preferably only one substituent group, preferably selected from alkyl (including haloalkyl such as $CF_3$, and preferably lower alkyl, more preferably lower acyclic alkyl, more preferably methyl), halogen (preferably fluoro or chloro), alkoxy (preferably lower alkoxy, more preferably lower acyclic alkoxy, more preferably methoxy).

Where $R_7$ is a substituted alkyl, $R_7$ is preferably alkyl substituted by a non-aromatic heterocyclic group or by aryl, and is preferably selected from aryl-substituted alkyl, particularly benzyl or pyridyl methyl (including (4-pyridyl) methyl, (3-pyridyl)methyl and (2-pyridyl)methyl) and preferably benzyl.

Where $R_7$ is a non-aromatic heterocyclic group, $R_7$ may be selected from 5 and 6-membered non-aromatic heterocyclic groups, preferably containing 1 or 2 heteroatoms, preferably only one heteroatom, and preferably selected from N, O and S, preferably N and O, and more preferably O. Preferably, said non-aromatic heterocyclic group is saturated.

In the compounds of formula (1), $R_8$ is selected from hydrogen, halogen, alkyl, aryl and non-aromatic heterocyclic groups. In one embodiment $R_8$ is selected from hydrogen, alkyl, aryl and non-aromatic heterocyclic groups. Preferably, $R_8$ is selected from hydrogen and alkyl, and is preferably hydrogen. Where $R_8$ is selected from alkyl, it is preferred that $R_8$ is selected from lower alkyl, and preferably acyclic lower alkyl.

In the compounds of formula (I), each of one or more pair(s) of the substituent groups $R_1$ to $R_6$ may together form a 3, 4, 5, 6, 7 or 8 membered ring, preferably a 3, 4, 5, or 6 membered ring. In one embodiment, each of one or more pair(s) of $R_1$ to $R_6$ may together form a 5, 6 or 7 membered ring, more preferably a 5 or 6 membered ring. It will be appreciated therefore that each of one or more pair(s) of substituent groups selected from $R_1$ and $R_2$; $R_3$ and $R_4$; and $R_5$ and $R_6$, may together form a 3, 4, 5, 6, 7 or 8 membered ring. It will also be appreciated that each of one or more pair(s) of groups selected from $R_1$ or $R_2$ together with $R_3$ or $R_4$; $R_1$ or $R_2$ together with $R_5$ or $R_6$; and $R_3$ or $R_4$ together with $R_5$ or $R_6$, may form a 3, 4, 5, 6, 7 or 8 membered ring.

Where a pair of the substituent groups $R_1$ to $R_6$ together form a ring, the ring may be saturated, partially unsaturated or aromatic, preferably saturated or partially unsaturated, and more preferably saturated. It will be appreciated that the formation of an aromatic ring by cyclisation of the substituent groups $R_1$ to $R_6$ is equivalent to the cyclisation of a plurality of pairs of these groups, for example cyclisation of $R_3$ and $R_4$ with $R_2$ and $R_1$ forms a pyridyl ring.

In the compounds of formula (1), a ring formed by a pair of the substituent groups $R_1$ to $R_6$ contains 0, 1 or 2 heteroatom(s). Where a ring is formed between $R_3$ and $R_4$, or between $R_5$ and $R_6$, or between $R_3$ or $R_4$ and $R_5$ or $R_6$, the ring may optionally contain one or two heteroatom(s). Where a ring is formed between $R_1$ and $R_2$, or between $R_1$ or $R_2$ and $R_3$ or $R_4$, or between $R_1$ or $R_2$ and $R_5$ or $R_6$, the ring may optionally contain one additional heteroatom. Preferably the heteroatoms are selected from N, O and S. Where a ring contains heteroatom(s), it is preferred that said ring contains only one heteroatom.

In one embodiment, $R_1$ and $R_2$ together form a 4, 5 or 6 membered ring, preferably a 5 or 6 membered ring, preferably saturated, and optionally containing one additional heteroatom, preferably N or O, and preferably O.

In one embodiment, $R_3$ and $R_4$ together form a 3, 4, 5 or 6-membered ring.

In one embodiment, $R_5$ and $R_6$ together form a 3, 4, 5 or 6-membered ring, preferably a 3 or 4-membered ring.

In one embodiment, $R_1$ or $R_2$ together with $R_3$ or $R_4$ form a 4, 5 or 6-membered ring.

In one embodiment, $R_1$ or $R_2$ together with $R_5$ or $R_6$ form a 4, 5 or 6-membered ring.

In one embodiment, $R_3$ or $R_4$ together with $R_5$ or $R_6$ form a 3-membered ring.

In one embodiment of the invention, the compound of formula (1) is selected from the group consisting of:

2-[2-(2-phenyl)adamantyl]ethylamine,
2-[2-[2-(2-thienyl)]adamantyl]ethylamine,
4-[2-[2-[2-(2-thienyl)]adamantyl]]ethylmorpholine,
1-[2-[2-[2-(2-thienyl)]adamantyl]]ethylpyrrolidine,
1-[2-[2-[2-(2-thienyl)]adamantyl]]ethylpiperidine,
N-(2-methylpropyl)-2-[2-[2-(2-thienyl)]adamantyl] ethylamine,
N-(4-methylbenzyl)-2-[2-[2-(2-thienyl)]adamantyl] ethylamine,
2-[2-[2-(4-methyl)phenyl]adamantyl]ethylamine,
N-methyl-2-[2-[2-(4-methylphenyl)]adamantyl]ethylamine,
N,N-dimethyl-2-[2-[2-(4-methylphenyl)]adamantyl] ethylamine,
2-[2-(2-methyl)adamantyl]ethylamine,
2-[2-(2-benzyl)adamantyl]ethylamine,
2-[2-(2-(3-methoxyphenyl))adamantyl]ethylamine, and
1-[2-[2-(4-methylphenyl)]adamantyl]-2-propylamine.

In a preferred embodiment, the compound of formula (1) is 2-[2-(2-phenyl)adamantyl]ethylamine.

It will be appreciated from the definition above that the compounds of formula (1) do not include compounds wherein either of the substituent groups $R_7$ or $R_8$ form cyclic moieties by cyclisation with each other or with any of $R_1$ to $R_6$. Equally, it will be appreciated that the compounds of formula (1) do not include compounds wherein either of $R_7$ or $R_8$ form cyclic moieties with any other part of the molecule. As noted above, compounds of formula (1) do, however, include compounds wherein either of $R_7$ or $R_8$ is itself a cyclic group, such as a cycloalkyl group or an aryl group.

The compounds of formula (1) may exist in a number of diastereomeric and/or enantiomeric forms. Reference in the present specification to "a compound of formula (1)" is a reference to all stereoisomeric forms of the compound and includes a reference to the unseparated stereoisomers in a mixture, racemic or non-racemic, and to each stereoisomer in its pure form.

The present invention also provides a method of treatment of conditions generally associated with abnormalities in glutamatergic transmission comprising administering to a patient an effective dose of a compound of the formula (1) as defined above, and pharmaceutically acceptable salts and prodrugs thereof.

The present invention also provides a compound of the formula (1) as defined above, and pharmaceutically acceptable salts thereof, per se, other than compounds wherein $R_7$ is 3-aminopropyl, preferably other than compounds wherein $R_7$ is an amino-substituted alkyl group, more preferably other than compounds wherein $R_7$ is an alkyl group substituted by a highly-polar or other non-lipophilic group and preferably other than compounds wherein $R_7$ is an alkyl group substituted by a substituent other than one selected from aryl and non-aromatic heterocycles.

In a preferred embodiment, the present invention provides a compound of the formula (1) as defined above, and pharmaceutically acceptable salts thereof, per se, wherein $R_7$ is selected from cycloalkyl, unsubstituted acyclic alkyl (preferably lower alkyl), acyclic alkyl (preferably lower alkyl) substituted by a non-aromatic heterocyclic group, acyclic alkyl (preferably lower alkyl) substituted by aryl, aryl and non-aromatic heterocyclic groups; preferably is selected from unsubstituted alkyl (preferably acyclic, preferably lower alkyl), alkyl (preferably acyclic, preferably lower alkyl) substituted by a non-aromatic heterocyclic group, alkyl (preferably acyclic, preferably lower alkyl) substituted by aryl, aryl, and non-aromatic heterocyclic groups; is preferably selected from unsubstituted alkyl (preferably acyclic, preferably lower alkyl), alkyl (preferably acyclic, preferably lower alkyl) substituted by a non-aromatic heterocyclic group, alkyl (preferably acyclic, preferably lower alkyl) substituted by aryl, and aryl; and is more preferably selected from unsubstituted alkyl (preferably acyclic and preferably lower alkyl), alkyl (preferably acyclic and preferably lower alkyl) substituted by aryl, and aryl. Where $R_7$ is selected from aryl or aryl-substituted alkyl, reference to said aryl specifically includes reference to heteroaromatic groups. Where $R_7$ is alkyl substituted by aryl, in a preferred embodiment $R_7$ is alkyl substituted by a carbocyclic aromatic group.

The present invention also provides, for use in therapy, a compound of the formula (1) as defined above and pharmaceutically acceptable salts and prodrugs thereof.

According to a further aspect of the present invention there is provided a method of preparing the compounds of the formula (1) as defined above. Compounds of formula (1) may be prepared by conventional routes for example according to the methods described in Reaction Schemes 1–7.

Compounds of formula (1) where $R_3$ and $R_4$ are both H (Reaction Scheme 1) may be prepared from amides (4) by standard methods such as reduction with borane. Amides (4) may be prepared from esters (5) by standard methods such as treatment with a suitable amine in the presence of trimethyl aluminium. Esters (5) may be prepared from esters (2) by standard methods such as alkylation in the presence of a strong base. Esters (5), where $R_5$ and $R_6$ together form a ring, may be prepared from esters (2) by standard methods such as double alkylation as described above. The preparation of esters (2) is described in the literature. Alternatively amides (4) may be prepared from amides (3) by standard methods such as alkylation as described above. Amides (3) may be prepare from esters (2) by standard methods such as reaction with a suitable amine in the presence of trimethyl aluminium as described above. Alternatively compounds of formula (1) where $R_3$, $R_4$, $R_5$ and $R_6$ are all H may be prepared directly from amides (3) by standard methods such as reduction as described above.

Reaction Scheme 1

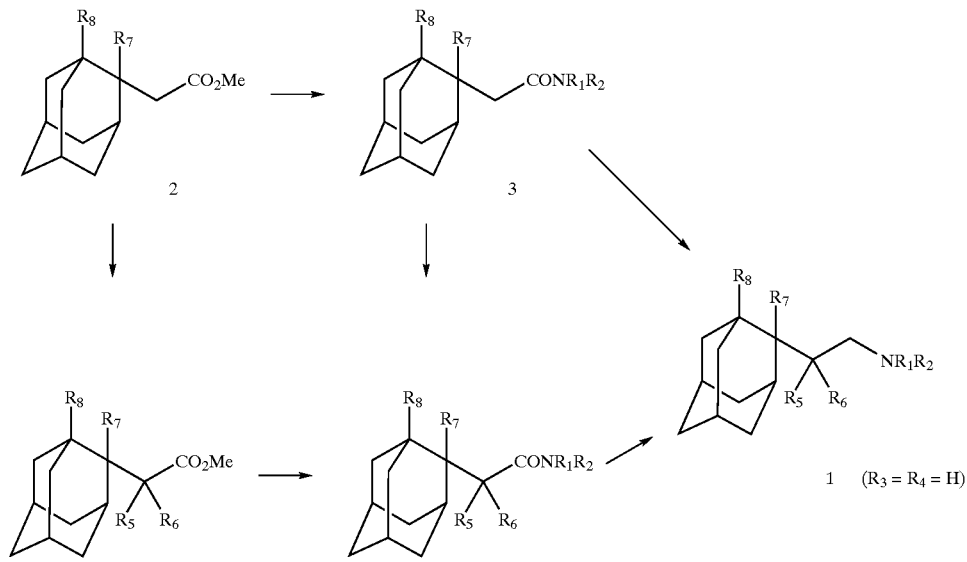

Compounds of formula (1) where $R_4$ is H (Reaction Scheme 2) may be prepared from ketones (6) by standard methods such as reductive amination with an appropriate amine. Ketones (6) may be prepared from alcohols (7) by standard methods such as oxidation (eg Swern oxidation). Alcohols (7) may be prepared from esters (5) by standard methods such as reduction with $LiAlH_4$. Alternatively compounds of formula (1) where $R_4$ is H may be prepared from amines (8) by standard methods such as alkylation, reductive alkylation or arylation. Amines (8) may be prepared from alcohols (7) by standard methods such as Mitsunobu reaction with phthalimide followed by deprotection with hydrazine.

standard methods such as Mitsunobu reaction followed by deprotection as described above. Alternatively, amines (9) may be prepared from alcohols (10) by standard methods such as converting the alcohol into a better leaving group such as a mesylate, followed by treatment with an azide salt and then reduction by standard methods such as Staudinger reaction. Alcohols (10), where $R_4$ is alkyl or aryl, may be prepared from ketones (6) by reaction with an appropriate Grignard reagent. Alcohols (10), where $R_4$ is H, may be prepared from ketones (6) by standard methods such as reduction with DIBAL. Alternatively, compounds of formula (1) may be prepared from alcohols (10) by standard methods such as converting the alcohol into a better leaving Reaction Scheme 2

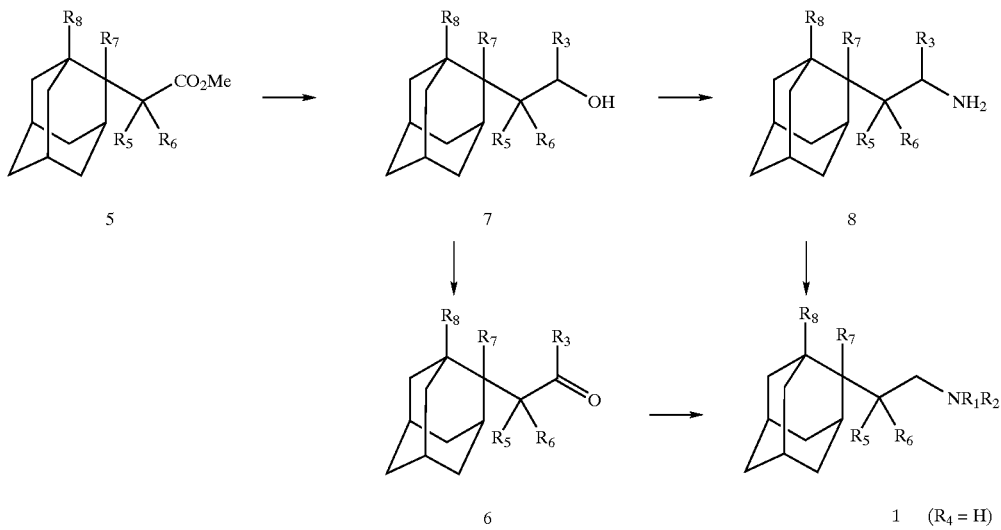

Compounds of formula (1) (Reaction Scheme 3) may be prepared from amines (9) by standard methods such as alkylation, reductive alkylation or arylation as described above. Amines (9) may be prepared from alcohols (10) by group as described above, followed by treatment with an appropriate amine.

Reaction Scheme 3

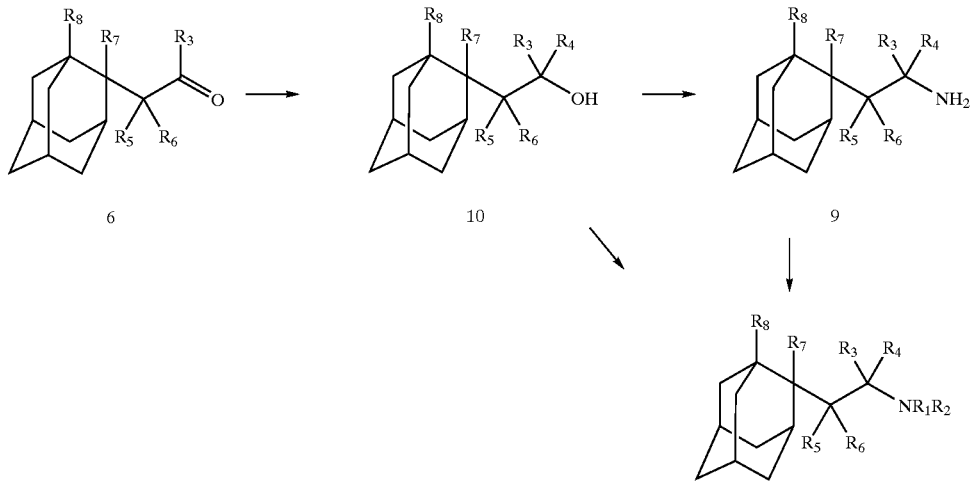

Compounds of formula (1), where $R_5$ is H may be prepared from amines (11) by standard methods such as alkylation, reductive alkylation or arylation as described above. Amines (11) may be prepared from nitro compounds (12) or (13) by standard methods such as reduction with $LiAlH_4$. Nitro compounds (12) may be prepared from nitro compounds (13) by standard methods such as alkylation in the presence of a base. Nitro compounds (12), where $R_3$ and $R_4$ together form a ring, may be prepared from nitro compounds (13) where $R_3$ is H, by standard methods such as double alkylation as described above. Nitro compounds (13) may be prepared from ketones or aldehydes (14) by standard methods such as condensation with a nitroalkane in the presence of a suitable base. Ketones (14), where $R_6$ is alkyl or aryl, may be prepared from nitrites (15) by standard methods such as treatment with a Grignard reagent or an alkyl or aryl lithium reagent. Aldehydes (14) where $R_6$ is H, may be prepared from nitriles (15) by standard methods such as reduction with DIBAL followed by hydrolysis of the intermediate imine. The preparation of nitrites (15) has been described in the literature.

Compounds of formula (1) where $R_3$, $R_4$ and $R_5$ are all H (Reaction Scheme 5) may be prepared from aldehydes (16) where $R_3$ is H, by standard methods such as reductive amination as described above. Aldehydes (16) where $R_3$ is H, may be prepared from aldehydes or ketones (14) by standard methods such as Wittig reaction with an α-alkoxymethyl phosphonium salt, followed by hydrolysis of the intermediate enol ether. Aldehydes and ketones (14) may be prepared as described above. Alternatively, compounds of formula (1) where $R_4$ and $R_5$ are H may be prepared from ketones (16), by standard methods such as reductive amination as described above. Ketones (16) may be prepared from aldehydes or ketones (14) as described above. Alternatively, compounds of formula (1) where $R_3$ and $R_5$ are both H may be prepared from ketones (17) by standard methods such as reductive amination as described above. Ketones (17) may be prepared from alcohols (18) by standard methods such as oxidation as described above. Alcohols (18), where $R_4$ is alkyl or aryl, may be prepared from aldehydes (16) where $R_3$ is H by standard methods such as treatment with an appropriate Grignard reagent.

Reaction Scheme 4

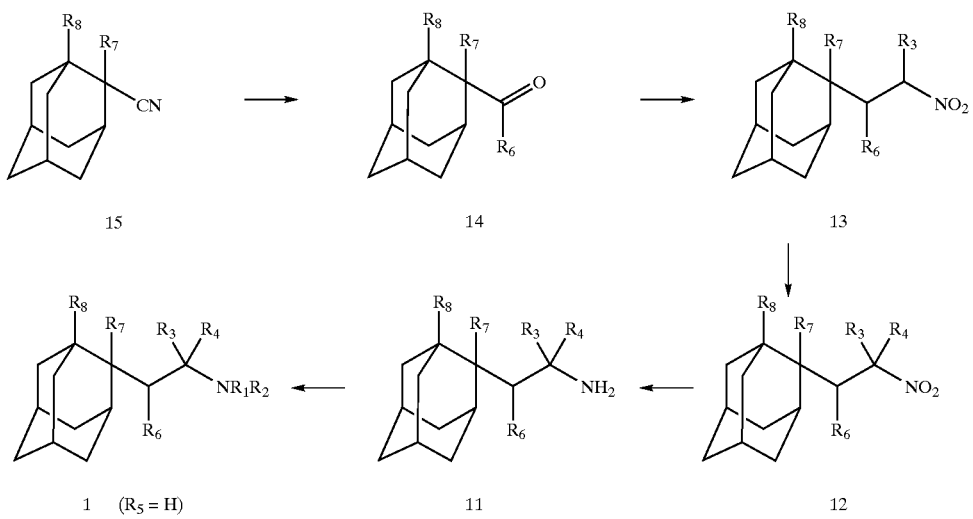

Reaction Scheme 5

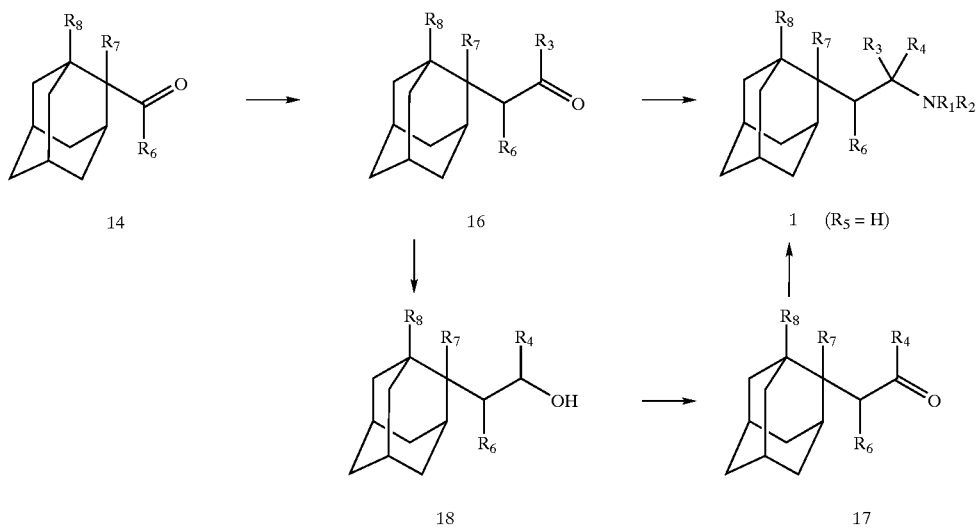

Compounds of formula (1) where $R_3$ an $R_4$ are both H (Reaction Scheme 6) may be prepared from amines (19) standard methods such as alkylation, reductive alkylation or arylation as described above. Amines (19) may be prepared from nitriles (20) by standard methods such as reduction with borane. Nitriles (20) may be prepared from nitrites (21) by standard methods such as alkylation as described above. Also, nitrites (20) where $R_5$ and $R_6$ together form a ring, may be prepared from nitrites (21) where $R_6$ is H, by standard methods such as double alkylation as described above. Nitrites (21) may be prepared from α-cyano esters (22) by deethoxycarbonylation. α-Cyano esters (22) may be prepared from α-cyano esters (23) by standard methods such as alkylation as described above. α-Cyano esters (23) may be prepared from unsaturated α-cyano esters (24) by conjugate addition of an appropriate organometallic reagent. The preparation of unsaturated α-cyano esters (24) is described in the literature. Alternatively, nitrites (20) where $R_5$ and $R_6$ are H may be prepared directly from α-cyano esters (23) by standard methods as described above.

Compounds of formula (1) where X is C (Reaction Scheme 7), may be prepared from amines (25) where X is C by standard methods such as alkylation, reductive alkylation or arylation as described above. Amines (25) where X is C may be prepared from nitro compounds (26) where X is C by standard methods such as reduction as described above. Nitro compounds (26) where X is C may be prepared from nitroalkenes (27) by standard methods such as treatment with diazomethane in the presence of a catalyst. Nitroalkenes (27) may be prepared from aldehydes or ketones (14) by standard methods such as condensation with a nitroalkane in the presence of a suitable base. Compounds of formula (1) where X is O, may be prepared from amines (25) where X is O by standard methods such as alkylation, reductive alkylation or arylation. Amines (25) where X is O may be prepared from nitro compounds (26) where X is O by standard methods such as reduction as described above. Nitro compounds (26) where X is O may be prepared from nitroalkenes (27) by standard methods such as epoxidation with m-chloroperbenzoic acid.

Reaction Scheme 6

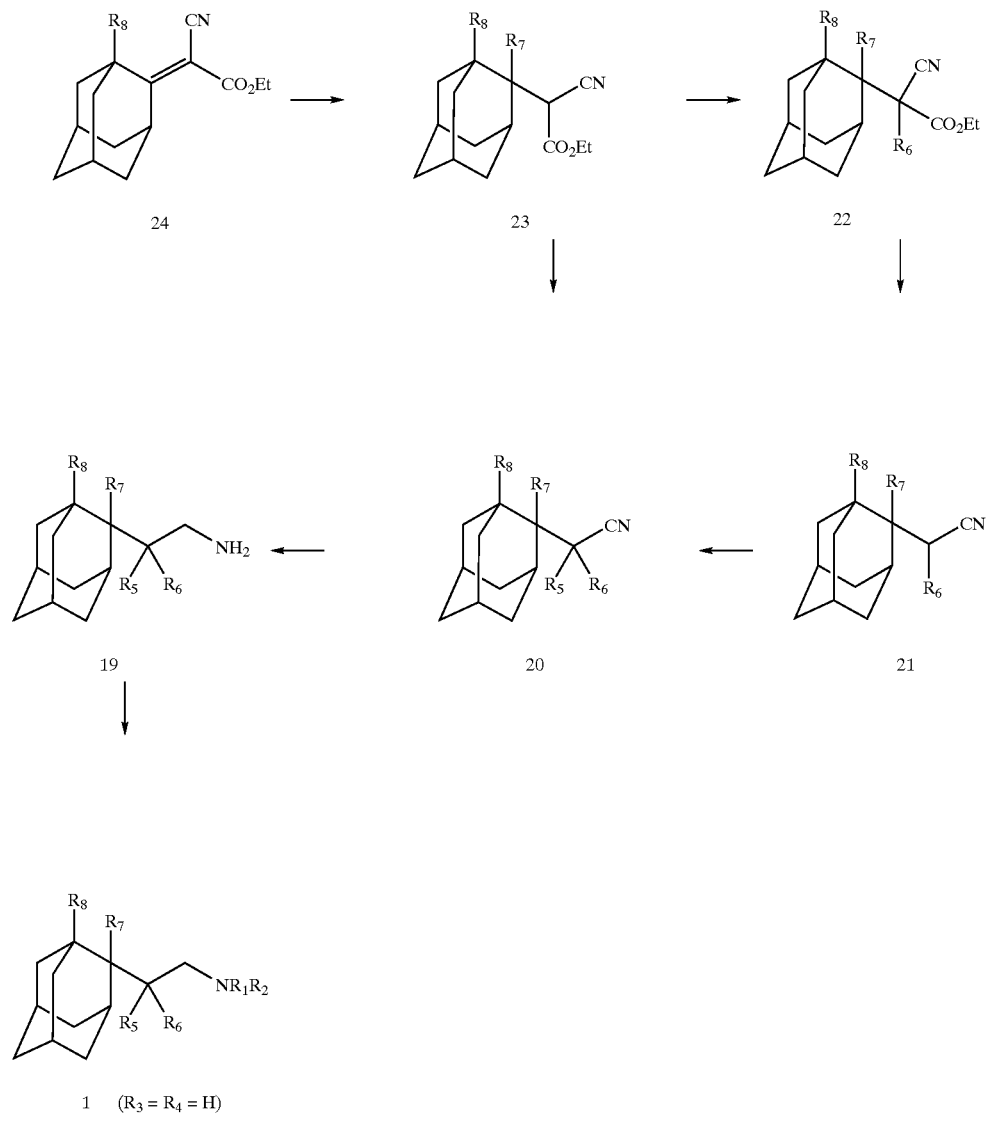

Reaction Scheme 7

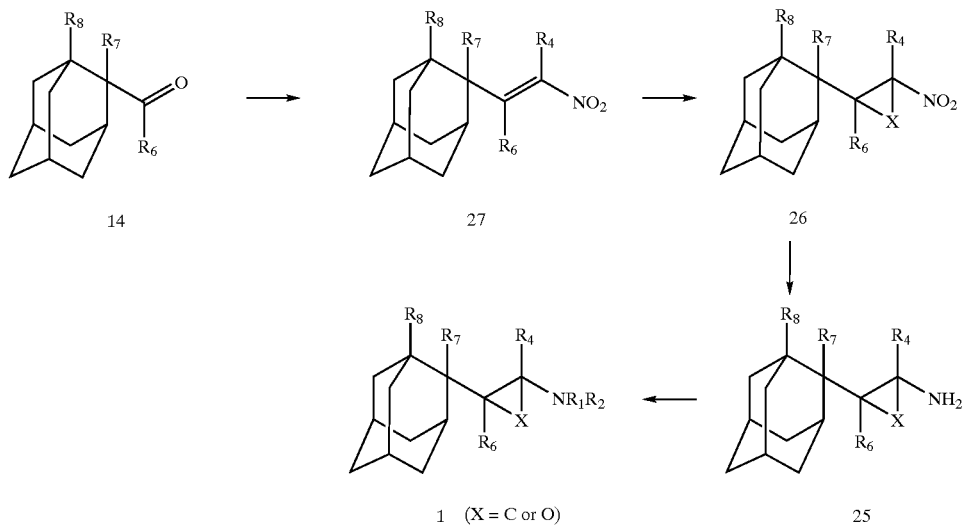

The present invention further provides a pharmaceutical composition comprising the compound of the formula (1), or pharmaceutically acceptable salts thereof, in combination with a pharmaceutically acceptable excipient.

The compound of formula (1) may be administered in a form suitable for oral use, for example a tablet, capsule, aqueous or oily solution, suspension or emulsion; for topical use including transmucosal and transdermal use, for example a cream, ointment, gel, aqueous or oil solution or suspension, salve, patch or plaster; for nasal use, for a example a snuff, nasal spray or nasal drops; for vaginal or rectal use, for example a suppository; for administration by inhalation, for example a finely divided powder or a liquid aerosol; for sub-lingual or buccal use, for example a tablet or capsule; or for parenteral use (including intravenous, subcutaneous, intramuscular, intravascular or infusion), for example a sterile aqueous or oil solution or suspension, or depot injection formulation. In general the above compositions may be prepared in a conventional manner using convention excipients, using standard techniques, including controlled release technologies, such as gelatin, lipid, gel depot, liposome and microcapsule based systems well known to those skilled in the art of pharmacy.

For oral administration, the compounds of the invention will generally be provided in the form of tablets or capsules or as an aqueous solution or suspension.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredient is mixed with water or an oil such as peanut oil, liquid paraffin or olive oil.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

Transdermal formulations include membrane permeation systems, multi-laminate adhesive dispersion systems and matrix dispersion systems. Transdermal delivery also includes the use of electrically aided transport and skin penetration enhancers.

The preferred route of administration will be as an intravenous infusion, preferably over a period of up to seven days, or as an oral formulation, or as an intramuscular injection via a styrette or as a subcutaneous injection.

It will be appreciated that the dosage levels used may vary over quite a wide range depending upon the compound used, the severity of the condition exhibited by the patient and the patient's body weight. However, without commitment to a rigid definition of dosages it may be stated that a daily dosage of the active constituent (estimated as the free base) is 100 $\mu$g to 800 mg. More particularly the preferred compounds may be administered at a preferred dose of 50–800 mg daily in single or divided doses.

The invention will now be described in detail. It will be appreciated that the invention is described by way of example only and modification of detail may be made without departing from the scope of the invention.

Experimental

I. Synthesis

HPLC retention times were recorded using a Perkin-Elmer 200-series with a 235C diode array detector: Column: Waters XTERRA RP18 5 $\mu$m (4.6 mm×50 mm); Mobile phase: MeOH/10 mM NH$_4$OAc aq (50/50 isocratic for 1 min, linear gradient to 80/20 over 5 min then 80/20 isocratic for 3 min); Flow rate: 2 mL/min; Detection wavelength $\lambda$=235 nm (unless otherwise stated).

EXAMPLE 1

2-[2-(2-Phenyl)adamantyl]ethylamine hydrochloride

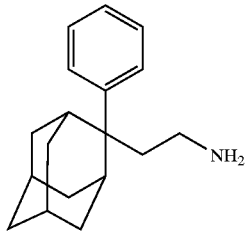

2-[2-(2-Phenyl)adamantyl]ethanol

A solution of methyl 2-phenyladamantyl-2-acetate (2.5 g, 8.8 mmol) in anhydrous THF (50 mL) at 0° C. was treated over 10 min with lithium aluminium hydride (0.8 g, 22 mmol), stirred at room temperature for 6 h, quenched by cautious addition of a 1:1 mixture of Rochelle's salt and saturated ammonium chloride (100 mL) and stirred for 12 h. The reaction mixture was partitioned between ether (200 mL) and water (100 mL), the organic phase was washed with brine, dried (MgSO$_4$), passed through a plug of silica and concentrated in vacuo to give the product (2.3 g, 98%) as a white solid: mp 116–117° C.; IR $\nu_{max}$ (Nujol)/cm$^{-1}$ 3277, 2924, 1493, 1459, 1377, 1042, 1030 and 703; NMR $\delta_H$(400 MHz, CDCl$_3$) 1.25 (1H, br m), 1.54 (2H, d, J 12.0 Hz), 1.70 (3H, s), 1.77 (2H, d, J 12.0 Hz), 1.85 (2H, d, J 13.0 Hz), 1.95 (1H, br s), 2.00 (2H, t, J 13.0 Hz), 2.27 (2H, d, J 13.0 Hz), 2.38 (2H, s), 3.32 (2H, t, J 7.5 Hz), 7.16–7.20 (1H, m) and 7.32–7.33 (4H, m); Anal. Calcd for C$_{18}$H$_{24}$O: C, 84.32; H, 9.43, Found: C, 84.19; H, 9.58.

2-[2-(2-Phenyl)adamantyl]ethylamine hydrochloride

A mixture of 2-[2-(2-phenyl)adamantyl]ethanol (1.0 g, 3.9 mmol), phthalimide (0.52 g, 3.9 mmol) and triphenylphosphine (1.0 g, 3.9 mmol) in anhydrous THF (50 mL) was treated with diethyl azodicarboxylate (0.68 g, 3.9 mmol), refluxed for 4 h, cooled to room temperature and concentrated in vacuo. The residue was partitioned between ethyl acetate (100 mL) and 1-M HCl (100 mL), the organic phase was washed with sodium bicarbonate then brine, dried (MgSO$_4$), filtered through a pad of silica and concentrated in vacuo to give a yellow oil consistent with N-[2-[2-(2-phenyl)adamantyl]]ethyl phthalimide. The crude product was treated with hydrazine hydrate (0.9 mL, 19.5 mmol) in ethanol (20 mL), refluxed for 18 h, concentrated in vacuo, treated with 1-M HCl in ether (10 mL), stirred for 20 min, concentrated in vacuo and the residue purified by chromatography [SiO$_2$; EtOAc-MeOH (4:1)] to give the title compound (0.54 g, 48%) as a pale solid: mp 278–281° C. dec; IR $\nu_{max}$ (Nujol)/cm$^{-1}$ 3845, 2922, 1600, 1510, 1458, 1377, 1126, 1100, 1032, 752 and 700; NMR $\delta_H$(400 MHz, CDCl$_3$) 1.51 (2H, d, J 12.0 Hz), 1.66–1.74 (8H, m), 1.91–1.97 (2H, m), 2.32–2.33 (4H, m), 2.40 (2H, s), 7.20 (1H, t, J 6.5 Hz), 7.31–7.36 (4H, m) and 7.83 (3H, br s); Anal. Calcd for C$_{18}$H$_{25}$N.HCl: C, 73.46; H, 8.91; N, 4.76. Found: C, 73.54; H, 8.92; N, 4.76.

EXAMPLE 2

2-[2-[2-(2-Thienyl)]adamantyl]ethylamine hydrochloride

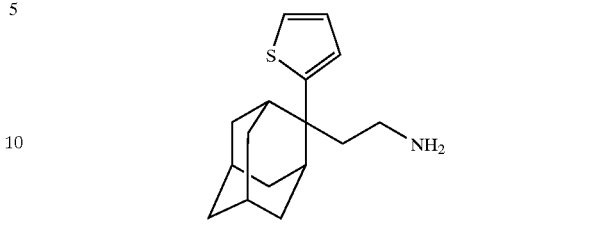

2,2-Dimethyl-5-[2-[2-(2-thienyl)]adamantyl]-1,3-dioxane-4,6-dione

A stirred solution of 5-(2-adamantylidene)-2,2-dimethyl-1,3-dioxane-4,6-dione (3.0 g, 10.9 mmol) in anhydrous THF (100 mL) was cooled to –78° C. under argon and treated with 2-thienyllithium (16.3 mL, 16.3 mmol) and stirred at –78° C. for 5 mins and allowed to warm to room temperature for 18 h. The reaction mixture was partitioned between diethyl ether (100 mL) and saturated ammonium chloride solution (100 mL), separated, dried (MgSO$_4$) and concentrated in vacuo to give a solid which was triturated with iso-hexane and dried in vacuo to afford the title compound (2.72 g, 69%) as an off-white solid: mp 164–169° C.; NMR $\delta_H$(400 MHz, CDCl$_3$) 0.90 (3H, s), 1.53 (3H, s), 1.70–1.76 (5H, m), 1.91–1.94 (2H, d, J 13.8 Hz), 2.03 (3H, br s), 2.36–2.39 (2H, d, J 13.7 Hz), 2.88 (2H, br s), 4.36 (1H, s), 6.84–6.85 (1H, d, J 3.5 Hz), 6.96–6.98 (1H, dd, J 3.6, 4.8 Hz) and 7.21–7.23 (1H, d, J 5 Hz); Retention time 3.97 min; Anal. Calcd for C$_{20}$H$_{25}$O$_4$S: C, 66.46; H, 6.97. Found: C, 65.93; H, 6.67.

Methyl [2-(2-thienyl)]adamantyl-2-acetate 2,2-Dimethyl-5-[2-[2-(2-thienyl)]adamantyl]-1,3-dioxane-4,6-dione (2.5 g, 6.92 mmol) and copper powder (0.100 g, 3.46 mmol) in pyridine (50 mL) and methanol (10 mL) were heated under reflux for 18 h. On cooling the reaction mixture was filtered through silica, concentrated in vacuo and the residue was washed with iso-hexane. The solid gained was purified by chromatography [SiO$_2$; iso-hexane—EtOAc (9:1)] to afford the title compound (1.69 g, 84%) as an off-white solid: mp 96.3–96.9° C.; NMR $\delta_H$(400 MHz, CDCl$_3$) 1.62–1.65 (2H, dd, J 1.2, 12.8 Hz), 1.74 (3H, s), 1.78–1.82 (2H, d, J 1.0, 13.6 Hz); 1.96 (1H, br s), 2.10–2.13 (2H, d, J 12 Hz), 2.21–2.24 (2H, d, J 13.6 Hz), 2.43 (2H, s), 2.80 (2H, s), 3.38 (2H, s), 6.78–6.79 (1H, dd, J 3.6, 1.2 Hz), 6.86–6.92 (1H, dd, J 3.6, 5 Hz) and 7.27–7.28 (1H, d, J 4.8, 1.2 Hz); Retention time 7.00 min; Anal. Calcd for C$_{17}$H$_{22}$O$_2$S: C, 70.31; H, 7.64. Found: C, 70.07; H, 7.64.

2-[2-[2-(2-Thienyl)]adamantyl]ethanol

This was prepared from methyl [2-(2-thienyl)]adamantyl-2-acetate using the method described in Example 1 to afford the title compound (1.38 g, 94%) as a white solid: mp 101.5–101.9° C.; NMR $\delta_H$(400 MHz, CDCl$_3$) 0.89 (1H, s), 1.59–1.61 (2H, d, J 12.8 Hz), 1.67–1.75 (5H, m), 1.94 (1H, br s), 2.06–2.11 (4H, m), 2.19 (2H, br s), 2.25–2.28 (2H, d, J 13.6 Hz), 3.37–3.41 (2H, t, J 7.4 Hz), 6.79–6.80 (1H, dd, J 0.8, 3.7 Hz), 6.92–6.94 (1H, dd, J 3.7, 5.8 Hz), 7.17–7.19 (1H, d, J 1, 5.4 Hz); Retention time 6.70 min; Anal. Calcd for C$_{16}$H$_{22}$OS: C, 73.24; H, 8.45. Found: C, 72.83; H, 8.63.

2-[2-[2-(2-Thienyl)]adamantyl]ethylamine hydrochloride

This was prepared from 2-[2-[2-(2-thienyl)]adamantyl] ethanol using the method described in Example 1 to afford the title compound (0.22 g, 22%) as a white solid: mp 250.6–251.9° C.; NMR $\delta_H$(400 MHz, CDCl$_3$) 1.62–1.65

(2H, d, J 13 Hz), 1.74–1.77 (6H, d, J 14.5 Hz), 1.97 (3H, s), 2.07–2.09 (2H, d, J 11.5 Hz), 2.16–2.26 (6H, m), 2.57 (2H, br s), 6.76–6.77 (1H, dd, J 0.9, 3.6 Hz), 6.92–6.94 (1H, dd, J 3.6, 5.4 Hz), 7.19–7.21 (1H, dd, J 0.8, 5.2 Hz) and 8.04 (3H, br s); Retention time 4.04 min; Anal. Calcd for $C_{16}H_{23}NS \cdot HCl \cdot 0.3H_2O$: C, 63.36; H, 8.18; N, 4.62. Found: C, 63.26; H, 8.12; N, 4.76.

EXAMPLE 3

4-[2-[2-[2-(2-Thienyl)]adamantyl]]ethylmorpholine hydrochloride

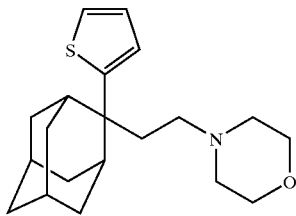

To a solution of 2-[2-[2-(2-thienyl)]adamantyl]ethanol (0.30 g, 1.14 mmol) in DCM (20 mL) was added triethylamine (0.16 mL, 1.14 mmol) and the solution was cooled to 0° C. Methanesulfonyl chloride (0.11 mL, 1.42 mmol) was added dropwise and the solution was stirred for 1 h and then was partitioned between DCM (50 mL) and water (50 mL). The organic phase was separated, dried (MgSO$_4$) and concentrated in vacuo to yield a solid. To a solution of the solid in DMF (5 mL) was added morpholine (0.15 mL, 1.71 mmol) and potassium carbonate (0.63 g, 4.56 mmol) and the reaction mixture was heated at 90° C. for 2 days. The mixture was partitioned between EtOAc (100 mL) and water (100 mL), separated, and the organic phase was washed with water, dried (MgSO$_4$) and concentrated in vacuo. The residue was purified by chromatography [SiO$_2$; iso-hexane—EtOAc (5:1-2:1)] to afford an oil which was dissolved in ether (10 mL) and 4-M HCl in dioxane (1 mL) was added. A precipitate formed which was collected and dried in vacuo to yield the title compound (0.099 g, 24%) as a white solid: mp 261.0–266.6° C.; NMR $\delta_H$(400 MHz, CDCl$_3$) 1.62–1.65 (2H, d, J 12.8 Hz), 1.72–1.79 (6H, m), 2.00–2.06 (3H, dd, J 12.8, 15 Hz), 2.15 (2H, s), 2.31–2.34 (3H, d, J 14 Hz), 2.56–2.63 (4H, m), 3.23–3.26 (2H, d, J 12.4 Hz), 3.84–3.88 (2H, dd, J 3.3, 13.2 Hz), 4.22–4.28 (2H, t, J 12.4 Hz), 6.78–6.79 (1H, dd, J 0.8, 3.7 Hz), 6.93–6.95 (1H, dd, J 3.7, 5.4 Hz), 7.21–7.22 (1H, d, J 5 Hz) and 12.0 (1H, br s); Retention time 6.60 min.

EXAMPLE 4

1-[2-[2-[2-(2-Thienyl)]adamantyl]]ethylpyrrolidine hydrochloride

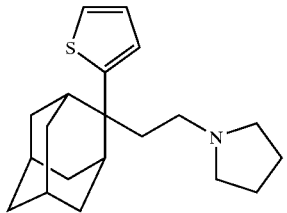

This was prepared from 2-[2-[2-(2-thienyl)]adamantyl]ethanol using the method described in Example 3 to afford the title compound (0.063 g, 16%) as a white solid: mp 223.4–224.1° C.; NMR $\delta_H$(400 MHz, CDCl$_3$) 1.62–1.65 (2H, d, J 13.2 Hz), 1.72–1.78 (4H, m), 1.91–2.13 (12H, m), 2.31–2.34 (4H, d, J 12.8 Hz), 2.46 (2H, s), 2.61 (2H, br s), 3.65–3.70 (2H, br s), 6.77–6.78 (1H, d, J 3.3 Hz), 6.92–6.94 (1H, dd, J 3.3, 5 Hz), 7.20–7.21 (1H, d, J 5.4 Hz) and 12.1 (1H, br s); Retention time 4.47 min.

EXAMPLE 5

1-[2-[2-[2-(2-Thienyl)]adamantyl]]ethylpiperidine hydrochloride

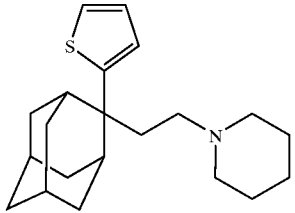

This was prepared from 2-[2-[2-(2-thienyl)]adamantyl]ethanol using the method described in Example 3 to afford the title compound (0.156 g, 38%) as a white solid: mp 269.5–270.0° C.; NMR $\delta_H$(400 MHz, CDCl$_3$) 1.27–1.33 (1H, m), 1.65–1.85 (10H, m), 1.99–2.06 (3H, dd, J 12.8, 16 Hz), 2.14 (2H, s), 2.21–2.41 (8H, m), 2.51 (2H, br s), 3.32–3.34 (2H, d, J 11 Hz), 6.77–6.78 (1H, dd, J 0.8, 3.3 Hz), 6.92–6.94 (1H, dd, J 3.3, 5 Hz), 7.19–7.21 (1H, dd, J 0.8, 5 Hz) and 12.1 (1H, br s); Retention time 5.23 min.

EXAMPLE 6

N-(2-Methylpropyl)-2-[2-[2-(2-thienyl)]adamantyl] ethylamine hydrochloride

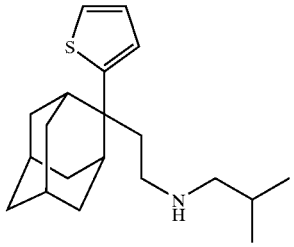

A solution of 2-[2-[2-(2-thienyl)]adamantyl]ethylamine hydrochloride (0.100 g, 0.34 mmol) and iso-butyraldehyde (0.021 mL, 0.23 mmol) in methanol (2 mL) was shaken at room temperature for 4 h. Amberlyst IRA-400 borohydride resin (0.27 g, 0.68 mmol) was added and the reaction mixture was shaken for a further 18 h. 4-Benzyloxybenzaldehyde polystyrene (0.42 g, 1.02 mmol) and DCM (2 mL) were added and the reaction mixture was shaken for 4 h, filtered, washed with DCM, and concentrated in vacuo to give a solid which was dissolved in ether (5 mL) and 4-M HCl in dioxane (0.5 mL) was added. A precipitate formed which was collected and dried in vacuo to yield the title compound (0.040 g, 48%) as a white solid: mp 204.9–205.4° C.; NMR $\delta_H$(400 MHz, CDCl$_3$) 0.99–1.00 (6H, d, J 7 Hz), 1.61–1.64 (3H, d, J 13.2 Hz), 1.72–1.75 (5H, d, 14.5 Hz), 1.97 (1H, s), 2.02–2.08 (3H, m), 2.14 (2H, s), 2.33–2.36 (4H, d, J 12 Hz), 2.47–2.49 (2H, dd, J 7, 12.8 Hz), 2.60 (2H, br s), 6.76–6.78 (1H, dd, J 0.8, 3.7 Hz), 6.91–6.93 (1H, dd, J 3.3, 5 Hz), 7.19–7.20 (1H, dd, J 0.8, 5 Hz) and 9.22 (2H, br s); Retention time 4.97 min.

EXAMPLE 7

N-(4-Methylbenzyl)-2-[2-[2-(2-thienyl)]adamantyl]ethylamine hydrochloride

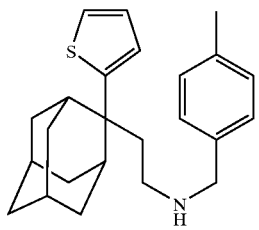

This was prepared from 2-[2-[2-(2-thienyl)]adamantyl]ethylamine hydrochloride using the method described in Example 6 to afford the title compound (0.013 g, 14%) as a white solid: mp 239.5–241.3° C.; NMR $\delta_H$(400 MHz, CDCl$_3$) 1.55–1.59 (3H, d, J 13.2 Hz), 1.69–1.71 (5H, d, J 9 Hz), 1.94–2.07 (5H, m), 2.24–2.34 (6H, m), 2.45 (2H, br s), 3.74 (2H, s), 6.63–6.64 (1H, d, J 3.1 Hz), 6.82–6.84 (1H, dd, J 3.7, 8.8 Hz), 7.08–7.13 (3H, dd, J 5, 8 Hz), 7.22–7.24 (5H, d, J 8 Hz) and 9.59 (2H, br s); Retention time 6.80 min.

EXAMPLE 8

2-[2-[2-(4-Methyl)phenyl]adamantyl]ethylamine hydrochloride

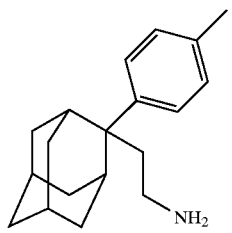

2-(4-Methylphenyl)adamantane-2-carboxaldehyde

A flame dried flask under argon was charged with 2-(4-methylphenyl)adamantane-2-carbonitrile (5.90 g, 23.5 mmol) and anhydrous ether (120 mL) and the solution was cooled to 0° C. Diisobutylaluminium hydride (47 mL, 46.9 mmol, 1-M in heptane) was added dropwise and the reaction left to warm to room temperature. After stirring for 1 h the reaction mixture was quenched with dilute HCl (20 mL) and then filtered through celite. The filtrate was partitioned between EtOAc (100 mL) and water (100 mL), separated, dried (MgSO$_4$) and concentrated in vacuo to afford the title compound (5.11 g, 86%) as a white solid: mp 93–97° C.: NMR $\delta_H$(400 MHz, CDCl$_3$) 1.61–1.64 (2H, d, J 12.8 Hz), 1.71 (2H, br s), 1.78–1.97 (8H, m), 2.33 (3H, s), 2.86 (2H, br s), 7.18–7.20 (2H, d, J 8.4 Hz), 7.25–7.27 (2H, dd, J 2, 8.4 Hz) and 9.27 (1H, s); Retention time 7.99 min ($\lambda$=220 nm).

2-(4-Methylphenyl)adamantyl-2-acetaldehyde

To a dark red stirred solution of 4-methoxymethyl triphenylphosphine chloride (8.08 g, 23.6 mmol) and potassium tert-butoxide (2.65 g, 23.6 mmol) in anhydrous THF under argon at room temperature was added 2-(4-methylphenyl)adamantane-2-carboxaldehyde (4.0 g, 15.7 mmol) in anhydrous THF, and the reaction mixture was left to stir for 5 h. The solvent was removed in vacuo, and the residue was partitioned between EtOAc and water. The organic phase was separated, washed with water and brine, dried (MgSO$_4$) and concentrated in vacuo to afford a yellow oil consistent with 2-(2-methoxy)ethenyl-2-(4-methyl)phenyladamantane.

2-(2-Methoxy)ethenyl-2-(4-methyl)phenyladamantane was dissolved in anhydrous THF and treated with 4-M HCl in dioxane (12 ml) and left to stir at room temperature for 18 h. The reaction mixture was concentrated in vacuo and purified by chromatography [SiO$_2$; iso-hexane—EtOAc (15:1)] to yield an oil which was triturated with iso-hexane to afford the title compound (2.60 g, 62%) as a white solid: mp 72–76° C.; NMR $\delta_H$(400 MHz, CDCl$_3$) 1.56–1.59 (2H, d, J 13.2 Hz), 1.72 (2H, s), 1.80–1.84 (2H, dd, J 13.6, 1.2 Hz), 1.91–1.98 (4H, m), 2.22–2.24 (2H, d, J 11.6 Hz), 2.33 (3H, s), 2.46 (2H, s), 2.72 (2H, s), 7.15–7.17 (2H, d, J 8.4 Hz), 7.24–7.26 (2H, d, J 7.6 Hz) and 9.31–9.33 (1H, t, J 3.2 Hz); Retention time 7.98 min.

N-Benzyl-2-[2-[2-(4-methylphenyl)]adamantyl]ethylamine hydrochloride

To a stirred solution of 2-(4-methylphenyl)adamantyl-2-acetaldehyde (0.20 g, 0.75 mmol) and benzylamine (0.081 mL, 0.75 mmol) in a mixture of acetic acid (0.5 mL) and MeOH (10 mL), was added, in one portion, sodium cyanoborohydride (0.047 g, 0.75 mmol) and the reaction left to stir at room temperature for 18 h. The reaction mixture was partitioned between EtOAc and 2-M NaOH and the organic phase was washed with water, brine, dried (MgSO$_4$) and concentrated in vacuo to afford an oil which was dissolved in ether (10 mL) and 4-M HCl in dioxane (1 mL) was added. A precipitate formed which was collected and dried in vacuo to yield the title compound (0.107 g, 36%) as an off-white solid: mp 234–239° C.; NMR $\delta_H$(400 MHZ, CDCl$_3$) 1.49–1.52 (3H, d, J 12.4 Hz), 1.73–1.80 (7H, m), 1.94 (1H, s), 2.24–2.30 (8H, m), 2.38 (2H, br s), 3.73 (2H, s), 7.04 (4H, m), 7.21–7.26 (5H, m) and 9.54 (2H, br s); Retention time 6.31 min ($\lambda$=220 nm).

2-[2-[2-(4-Methylphenyl)]adamantyl]ethylamine hydrochloride

A suspension of N-benzyl-2-[2-[2-(4-methylphenyl)]adamantyl]ethylamine hydrochloride (0.095 g, 0.24 mmol) and palladium on carbon (10%) in methanol (5 mL) was placed under an atmosphere of hydrogen for 48 h. The reaction mixture was filtered through a pad of celite and concentrated in vacuo to afford a solid which was dissolved in ether (5 mL) and 4-M HCl in dioxane (0.5 mL) was added. A precipitate formed which was collected and dried in vacuo to yield the title compound (0.044 g, 60%) as a white solid: 196–200° C.; NMR $\delta_H$(400 MHz, CDCl$_3$) 1.49–1.52 (2H, d, J 12 Hz), 1.66–1.73 (7H, m), 1.90–1.95 (3H, m), 2.18–2.36 (9H, m), 7.15–7.21 (4H, dd, J 8, 14.4 Hz) and 7.73 (3H, br s); Retention time 5.68 min ($\lambda$=220 nm).

EXAMPLE 9

N-Methyl-2-[2-[2-(4-methylphenyl)]adamantyl]ethylamine hydrochloride

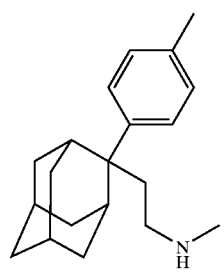

This was prepared from 2-(4-methylphenyl)adamantyl-2-acetaldehyde using the method described in Example 8 to afford the title compound (0.025 g, 10%) as a white solid: mp 258.1–260.8° C.; NMR $\delta_H$(400 MHz, CDCl$_3$) 1.54–1.57 (3H, d, J 9.6 Hz), 1.70–1.86 (7H, m), 1.97 (1H, s), 2.18–2.33

(8H, m), 2.39 (3H, br s), 2.46 (2H, br s), 7.13 (4H, s) and 9.23 (2H, br s); Retention time 5.33 min (λ=220 nm).

EXAMPLE 10

N,N-Dimethyl-2-[2-[2-(4-methylphenyl)]adamantyl]ethylamine hydrochloride

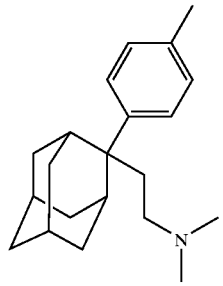

This was prepared from 2-(4-methylphenyl)adamantyl-2-acetaldehyde using the method described in Example 8 to afford the title compound (0.022 g, 31%) as a white solid: mp 236.0–236.5° C.; NMR $\delta_H$(400 MHz, CDCl$_3$) 1.55–1.60 (2H, m), 1.70–1.85 (7H, m), 2.00 (1H, br s), 2.19 (2H, m), 2.25–2.35 (7H, m), 2.51–2.56 (8H, m), 7.14 (4H, s) and 12.38 (1H, br s); Retention time 5.65 min (λ=220 nm).

EXAMPLE 11

2-[2-(2-Methyl)adamantyl]ethylamine hydrochloride

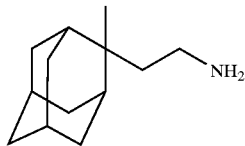

2,2-Dimethyl-5-[2-(2-methyl)adamantyl]-1,3-dioxane-4,6-dione

To a stirred solution of methylmagnesium bromide (1.4-M in THF/toluene, 7.75 mL, 10.86 mmol) in anhydrous THF (10 mL) under argon at −2° C. was added 5-(2-adamantylidene)-2,2-dimethyl-1,3-dioxane-4,6-dione (1.0 g, 3.61 mmol) in anhydrous THF (30 mL) dropwise over 10 min. The reaction mixture was allowed to warm to room temperature and stirred for a further 1 h. Then the reaction mixture was poured into 1-M HCl (100 mL) at 0° C., and was allowed to warm to room temperature. The aqueous phase was extracted with ethyl acetate (2×60 mL), and the organic phase was separated, washed with water (2×50 mL) and brine (50 mL), dried (MgSO$_4$) and concentrated in vacuo to afford the title compound (0.98 g, 93%) as a white solid: mp 150° C.; IR $\nu_{max}$ (DR)/cm$^{-1}$ 3346, 2921, 2644, 1749, 1464, 1393, 1294, 1118, 1084 and 966; NMR $\delta_H$(400 MHz, CDCl$_3$) 1.14 (3H, s), 1.67–1.75 (11H, m), 1.83–1.96 (4H, m), 2.04–2.08 (3H, m), 2.15 (2H, d, J 13.5 Hz) and 4.18 (1H, s).

Methyl 2-methyladamantyl-2-acetate

This was prepared from 2,2-dimethyl-5-[2-(2-methyl)adamantyl]-1,3-dioxan-4,6-dione using the method described in Example 2 to afford the title compound (0.57 g, 81%) as an orange oil; IR $\nu_{max}$(DR)/cm$^{-1}$ 2925, 2665, 1743, 1447, 1382, 1325, 1270, 1236, 1177, 1103 and 1010; NMR $\delta_H$(400 MHz, CDCl$_3$) 1.15 (3H, s), 1.56–1.62 (6H, m), 1.69 (2H, s), 1.84 (2H, m), 2.08 (4H, d, J 13.0 Hz), 2.52 (2H, s) and 3.64 (3H, s).

2-[2-(2-Methyl)adamantyl]ethanol

This was prepared from methyl 2-methyladamantyl-2-acetate using the method described in Example 1 to afford the title compound (0.40 g, 82%) as a white solid: mp 73.7–74.3° C.; IR $\nu_{max}$ (DR)/cm$^{-1}$ 3925, 3243, 2937, 2054, 1465, 1377, 1236, 1139, 1097, 1053, 919 and 861; NMR $\delta_H$(400 MHz, CDCl$_3$) 1.07 (3H, s), 1.11 (1H, s), 1.41 (2H, m), 1.52–1.58 (4H, m), 1.68 (2H, s), 1.81 (4H, m), 2.09 (4H, m) and 3.71 (2H, t, J 8.0 Hz).

2-[2-(2-Methyl)adamantyl]ethylamine hydrochloride

This was prepared from 2-[2-(2-methyl)adamantyl]ethanol using the method described in Example 1 to afford the title compound (0.28 g, 62%) as a white solid: mp 297.1–297.6° C.; IR $\nu_{max}$ (DR)/cm$^{-1}$ 3461, 2932, 1989, 1599, 1463, 1380, 1352, 1235, 1164, 1133, 1055, 950 and 766; NMR $\delta_H$(400 MHz, CDCl$_3$) 1.06 (3H, s), 1.41 (2H, s), 1.55 (4H, d, J 12.5 Hz), 1.67 (1H, s), 1.83 (2H, m), 1.97–2.09 (7H, m), 3.00 (2H, m) and 8.28 (3H, br s); NMR $\delta_C$(100 MHz, CDCl$_3$) 23.55, 27.39, 27.99, 32.85, 32.98, 35.45, 35.91, 36.42, 37.07 and 39.28.

EXAMPLE 12

2-[2-(2-Benzyl)adamantyl]ethylamine hydrochloride

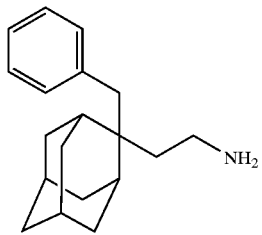

Ethyl 2'-[2-(2-benzyl)adamantyl]-2'-cyanoacetate

To a stirred solution of copper (I) bromide in anhydrous THF (12 mL) under argon at −2° C. was added benzylmagnesium bromide (2.0-M in THF, 5.14 mL, 10.29 mmol) and the reaction mixture was stirred for 10 min. Then ethyl 2'-cyanoadamantylidene-2-acetate (1.26 g, 5.14 mmol) in anhydrous THF (25 mL) was added dropwise over 5 min. The reaction mixture was allowed to warm to room temperature and stirred for a further 16 h. Then the reaction mixture was poured into 1-M HCl (100 mL) at 0° C., and was allowed to warm to room temperature. The aqueous phase was extracted with ethyl acetate (2×75 mL), and the organic phase was separated, washed with water (2×50 mL) and brine (50 mL), dried (MgSO$_4$) and concentrated in vacuo to yield a solid which was triturated with iso-hexane to afford the title compound (0.90 g, 52%) as a white solid: mp 89.9–90.8° C.; IR $\nu_{max}$ (DR)/cm$^{-1}$ 3446, 2916, 2669, 2243, 1733, 1601, 1579, 1494, 1458, 1393, 1369, 1243, 1116, 1098, 1035, 948 and 926; NMR $\delta_H$(400 MHz, CDCl$_3$) 1.16 (3H, t, J 7.0 Hz), 1.78–1.85 (6H, m), 1.94–2.01 (4H, mn), 2.10 (1H, br s), 2.40 (2H, m), 2.70 (1H, m), 2.97 (2H, d, J 14.6 Hz), 3.41 (1H, d, J 14.6 Hz), 3.60 (1H, m), 3.77 (1H, m), 4.36 (1H, s) and 7.22–7.28 (5H, m); m/z 338 (MH$^+$).

2-Benzyladamantyl-2-acetonitrile

Ethyl 2'-[2-(2-benzyl)adamantyl]-2'-cyanoacetate (0.19 g, 0.56 mmol), DMSO (1 mL), water (0.1 mL) and sodium chloride (0.020 g, 0.28 mmol) were heated at 145° C. for 2 h. After cooling the reaction mixture was diluted with water (25 mL) and extracted with ethyl acetate (2×25 mL). The organic phase was separated, washed with brine (25 mL), dried (MgSO$_4$) and concentrated in vacuo to yield an oil which was purified by chromatography [SiO₂; iso-hexane—Et₂O (10:1)] to afford the title compound (0.065 g, 43%) as a white solid: mp 96.2–97.5° C.; IR $v_{max}$ (DR)/cm⁻¹ 3061, 3027, 2920, 2669, 2246, 1981, 1957, 1931, 1878, 1813, 1600, 1494, 1482, 1466, 1355, 1344, 1299, 1220, 1177, 1100, 1083 and 1027; NMR $\delta_H$(400 MHz, CDCl₃) 1.69–1.78 (8H, m), 1.86–1.91 (3H, m), 2.01 (1H, br s), 2.36 (2H, br s), 2.40 (2H, s), 3.07 (2H, s) and 7.24–7.32 (5H, m); m/z 266 (MH⁺).

2-[2-(2-Benzyl)adamantyl]ethylamine hydrochloride

To a stirred solution of 2-benzyladamantyl-2-acetonitrile (0.055 g, 0.22 mmol) in anhydrous THF (4 mL) under argon was added 1-M borane-THF (0.55 mL, 0.55 mmol) and the reaction mixture was heated under reflux for 5 h and then stirred at room temperature for 12 h. The reaction mixture was cooled in ice/water and methanol (15 mL) was added. After stirring at room temperature for 15 min the mixture was concentrated in vacuo. Then 6-M hydrochloric acid was added carefully and the reaction mixture was heated at 90° C. for 2 h. After cooling to room temperature the reaction mixture was extracted with CHCl₃ (3×20 mL) washed with brine (25 mL), dried (MgSO₄) and concentrated in vacuo to afford the title compound (0.063 g, 99%) as a white solid: mp 195.8–196.8° C.; IR $v_{max}$ (DR)/cm⁻¹ 3254, 2904, 1955, 1601, 1493, 1465, 1394, 1353, 1227, 1100, 1029 and 953; NMR $\delta_H$(400 MHz, CDCl₃) 1.50–1.74 (8H, m), 1.82–1.87 (3H, m), 2.00 (3H, t, J 14.0 Hz), 2.33 (2H, d, J 13.5 Hz), 2.84–2.90 (4H, m), 7.16 (3H, m), 7.29 (2H, m) and 8.20 (3H, br s); m/z 270 (MH⁺).

EXAMPLE 13

2-[2-(2-(3-Methoxyphenyl))adamantyl]ethylamine hydrochloride

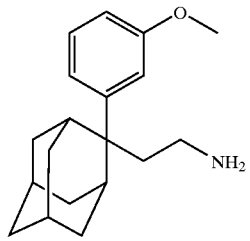

2,2-Dimethyl-5-[2-(2-(3-methoxyphenyl)adamantyl)]-1,3-dioxan-4,6-dione

This was prepared from 5-(2-adamantylidene)-2,2-dimethyl-1,3-dioxane-4,6-dione using the method described in Example 12 to afford the title compound (2.76 g, 82%) as a white solid: mp 142.5–143.4° C.; IR $v_{max}$ (DR)/cm⁻¹ 3493, 2996, 2856, 2654, 1768, 1745, 1595, 1495, 1468, 1421, 1388, 1282, 1119, 1100, 1043 and 1007; NMR $\delta_H$(400 MHz, CDCl₃) 0.71 (3H, s), 1.48 (3H, s), 1.65–1.73 (5H, m), 1.82 (2H, m), 1.94 (2H, d, J 13.2 Hz), 2.04 (1H, m), 2.37 (2H, d, J 12.5 Hz), 2.99 (1H, br s), 2.77 (3H, s), 4.28 (1H, s), 6.77–6.81 (2H, m), 6.84 (1H, d, J 8.0 Hz) and 7.25 (1H, t, J 8.0 Hz).

Methyl 2-(3-Methoxyphenyl)adamantyl-2-acetate

This was prepared from 2,2-dimethyl-5-[2-(2-(3-methoxyphenyl)adamantyl)]-1,3-dioxan-4,6-dione using the method described in Example 2 to afford the title compound (0.69 g, 56%) as a white solid: mp 91.2–91.3° C.; IR $v_{max}$ (DR)/cm⁻¹ 3414, 3082, 3053, 2943, 2668, 2102, 1920, 1726, 1583, 1457, 1246, 1176, 1057, 1019 and 982; NMR $\delta_H$(400 MHz, CDCl₃) 1.57 (2H, d, J 12.4 Hz), 1.71 (3H, br s), 1.82 (2H, d, J 12.2 Hz), 1.88–1.96 (3H, m), 2.21 (2H, d, J 13.0 Hz), 2.58 (2H, br s), 2.77 (2H, s), 3.31 (3H, s), 3.79 (3H, s), 6.72 (1H, dd, J 2.5, 7.5 Hz), 6.87 (1H, t, J 2.1 Hz), 6.90 (1H, d, J 7.0 Hz) and 7.23 (1H, t, J 8.0 Hz).

2-[2-(2-(3-Methoxyphenyl)adamantyl)]ethanol

This was prepared from methyl 2-(3-methoxyphenyl)adamantyl-2-acetate using the method described in Example 1 to afford the title compound (0.26 g, 95%) as a colourless oil; IR $v_{max}$ (DR)/cm⁻¹ 3355, 3075, 2922, 2670, 1604, 1487, 1485, 1287, 1255, 1174, 1107 and 1046; NMR $\delta_H$(400 MHz, CDCl₃) 0.80 (1H, br s), 1.53 (2H, d, J 9.5 Hz), 1.69 (3H, br s), 1.75 (2H, d, J 13.2 Hz), 1.85–2.03 (5H, m), 2.26 (2H, d, J 12.5 Hz), 2.33 (2H, d, J 11.5 Hz), 3.33 (2H, t, J 7.5 Hz), 3.81 (3H, s), 6.72 (1H, dd, J 2.0, 8.0 Hz), 6.88 (1H, t, J 2.0 Hz), 6.91 (1H, d, J 7.5 Hz) and 7.25 (1H, t, J 8.0 Hz).

2-[2-(2-(3-Methoxyphenyl)adamantyl)]ethylamine hydrochloride

This was prepared from 2-[2-(2-(3-methoxyphenyl)adamantyl)]ethanol using the method described in Example 1 to afford the title compound (0.035 g, 24%) as a light brown sticky solid; NMR $\delta_H$(400 MHz, CDCl₃) 1.53 (2H, d, J 9.5 Hz), 1.67–1.88 (7H, m), 1.94 (1H, br s), 2.09 (2H, m), 2.20 (2H, d, J 12.0 Hz), 2.28 (2H, d, J 10.0 Hz), 2.48 (2H, m), 3.80 (3H, s), 6.72 (1H, dd, J 2.2, 8.2 Hz), 6.78 (1H, t, J 2.0 Hz), 6.81 (1H, d, J 7.9 Hz), 7.24 (1H, t, J 8.0 Hz) and 7.93 (3H, br s); m/z 286 (MH⁺); Retention time 3.90 min (λ=220 nm).

EXAMPLE 14

1-[2-[2-(4-Methylphenyl)]adamantyl]-2-propylamine hydrochloride

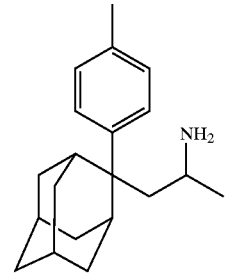

1-[2-[2-(4-Methylphenyl)]adamantyl]-2-propanol

A solution of 2-(4-methylphenyl)adamantyl-2-acetaldehyde (0.268 g, 1 mmol) in THF (4 mL) was placed under an atmosphere of argon and then cooled to 0° C. Methylmagnesium bromide (1.4-M in toluene/THF, 0.75 mL, 1.05 mmol) was then added dropwise and the solution stirred for 2.5 h. The reaction mixture was quenched with saturated aqueous ammonium chloride solution (10 mL) and allowed to warm to room temperature. The mixture was extracted with EtOAc (2×20 mL) and the combined organic layers washed with brine (10 mL), dried (MgSO₄) and concentrated in vacuo and purified by chromatography [SiO₂; heptane—EtOAc (9:1)] to afford the title compound (0.21 g, 74%) as a colourless oil: NMR $\delta_H$(400 MHz, CDCl₃) 0.63 (1H, d, J 3 Hz), 0.99 (3H, d, J 6 Hz), 1.50–1.61 (2H, m), 1.69–1.76 (6H, m), 1.83 (1H, dd, J 2.5, 12.5 Hz), 1.92–2.01 (3H, m), 2.16 (1H, dd, J 3, 13 Hz), 2.29 (1H, dd, J 3, 13 Hz), 2.32 (3H, s), 2.42 (2H, d, J 13 Hz), 3.55–3.61 (1H, m) 7.15–7.20 (2H, m), 7.23 (1H, d, J 2.5 Hz) and 7.30 (1H, dd, J 2.5, 9 Hz).

1-[2-[2-(4-Methylphenyl)]adamantyl]-2-propanone

To a solution of 1-[2-[2-(4-methylphenyl)]adamantyl]-2-propanol (0.21 g, 0.74 mmol) in CH₂Cl₂ (5 mL), under an atmosphere of argon, was added 4-methylmorpholine-N- oxide (0.257 g, 2.2 mmol) and powdered 4 Å molecular sieves (0.3 g). The mixture was stirred for 5 minutes and then tetrapropylammonium perruthenate (0.026 g, 0.074 mmol) was added. The mixture was stirred for a further 1.25 h and then filtered through a plug of silica, eluting with 10% EtOAc/heptane. The solvent was removed in vacuo to yield the title compound (0.195 g, 93%) as a white solid: NMR $\delta_H$(400 MHz, CDCl$_3$) 1.34 (3H, s), 1.54 (3H, s), 1.56 (1H, s), 1.70 (3H, br s), 1.80 (2H, dd, J 1.5, 13 Hz), 1.87 (2H, dd, J 1.5, 13 Hz), 1.95 (1H, br s), 2.25 (2H, dd, J 1.5, 13.5), 2.32 (3H, s), 2.54 (2H, br s), 2.76 (2H, s), 7.12 (2H, d, J 8 Hz) and 7.19 (2H, J 8 Hz); Retention time: 6.85 min ($\lambda$=220–269 nm); m/z 300.26 (M+NH$_4^+$), 283.25 (MH$^+$).

1-[2-[2-(4-Methylphenyl)]adamantyl]-2-propylamine hydrochloride

To a solution of 1-[2-[2-(4-methylphenyl)]adamantyl]-2-propanone (0.195 g, 0.69 mmol) in 10% acetic acid/1,2 dichloroethane (4 mL) was added ammonium acetate (0.106 g, 1.38 mmol) and polymer supported cyanoborohydride (0.298 g, 1.38 mmol). The reaction was stirred at room temperature for 24 h and then the temperature was raised to 50° C. for a further 48 h. The mixture was allowed to cool to room temperature, poured onto an Isolute SCX-2 cartridge (5 g), washed with methanol and then 2M ammonia in methanol. The second fraction was concentrated in vacuo to yield a colourless oil which was dissolved in CH$_2$Cl$_2$ (4 mL) and then 4-M HCl in dioxane (0.24 mL) was added. Diisopropylether (5 mL) was added and a white precipitate formed which was collected and dried in vacuo to yield the title compound (0.133 g, 60%) as a white solid: m.p. 344–346° C.; NMR $\delta_H$(400 MHz, DMSO) 0.69 (3H, d, J 6.5 Hz), 1.51 (2H, t, J 11 Hz), 1.65–1.81 (7H, m), 1.84 (1H, dd, J 9.5, 14 Hz), 1.90 (1H, br s), 2.03 (1H, dd, J 2, 14 Hz), 2.17 (1H, d, J 14 Hz), 2.26 (1H, d, J 14 Hz), 2.29 (3H, s) 2.39 (2H, br s), 2.50–2.52 (6H, m), 2.58 (1H, br s), 3.35 (4H, br s), 7.16–7.26 (4H, m) and 7.60 (3H, br s); Retention time 5.09 min ($\lambda$=220 nm); mz 284.32 (MH$^+$).

II. NMDA Receptor Binding

The NMDA receptor contains several distinct binding domains that can regulate opening of the cationic channel. The phencyclidine (PCP) site of the NMDA receptor can be radiolabeled with [$^3$H]-(+)-5-methyl-10,11-dihydro-5H-dibenzo[a,d]cyclohepten-5,10-imine hydrogen maleate, [$^3$H-MK-801]. The following describes the procedure for determining the affinity of compounds for the PCP site in rat cortical membranes.

Frozen rat cortex, homogenized in 10 volumes of ice-cold 0.32-M sucrose is centrifuged at 1,000 g for 12 min and the supernatant stored on ice whilst the pellet is resuspended, rehomogenized and recentrifuged twice more. The three final supernatants are pooled and centrifuged at 30,000 g for 40 min at 4° C. to yield P2 pellets. These are resuspended in ice-cold distilled water, and centrifuged at 30,000 g for 50 min at 4° C. Following three further washes in distilled water, the P2 pellets are stored at −20° C. for at least 18 h. On the day of the assay, membrane pellets are thawed at room temperature, resuspended in ice-cold distilled water and centrifuged at 30,000 g for 20 min. The pellets are resuspended in 50-mM tris-HCl (pH:7.4) and recentrifuged twice more before being resuspended in tris-HCl for immediate use in the assay. Binding assays are performed at equilibrium in a total volume of 200 µL, containing [$^3$H]-MK-801 (5-nM final conc.), 10-µM glutamate, 10-µM glycine, 160 µL of membrane preparation and additional drugs where appropriate. Non-specific binding is determined using MK-801 (10-µM). The assay is incubated for 120 min at room temperature. The incubation is terminated by rapid filtration through Whatman GF/B filters (pre-soaked in 0.1% PEI solution). The assay tubes and filters are washed five times with 1 mL of ice-cold assay buffer. The filters are placed in poly-Q mini vials with approximately 5 mL of scintillation fluid. The vials are then shaken and left for at least 8 h before being counted on a liquid scintillation counter. To determine the free ligand concentration 3 aliquots (20 µL) of the [$^3$H]-MK-801 working solution are also counted. Concentration response data for drugs is analysed using a 4 parameter equation fitted by non-linear regression. This yields the half maximally effective drug concentration (IC$_{50}$) and Hill coefficient.

TABLE 1

Potency of test compounds to displace [$^3$H]-MK-801 from rat cortical homogenates.

| Compound | IC$_{50}$ (µM) |
| --- | --- |
| Memantine | 6.50 ± 0.94 |
| Ketamine | 6.51 ± 4.54 |
| Example 1 | 1.09 ± 0.40 |
| Example 2 | 2.70 ± 0.54 |

III. Assessment of Side-Effect Liability (PCP Syndrome)

Side effect liability was assessed by utilising a standardised ethnological rating of behaviours recognised to be elicited by prototypical psychotomimetic NMDA receptor channel blockers such as phencyclidine and aptiganel (Cerestat™), similar to those reported by Martin et al., Life Sci 1979 24:1699–1703. Groups of eight male Sprague Dawley rats weighing 250–280 g. were placed in Plexiglass chambers and administered test compounds. After 20 minutes the percentage of rats in each group showing the behaviours noted in Table 2 was rated.

TABLE 2

Figure 2:
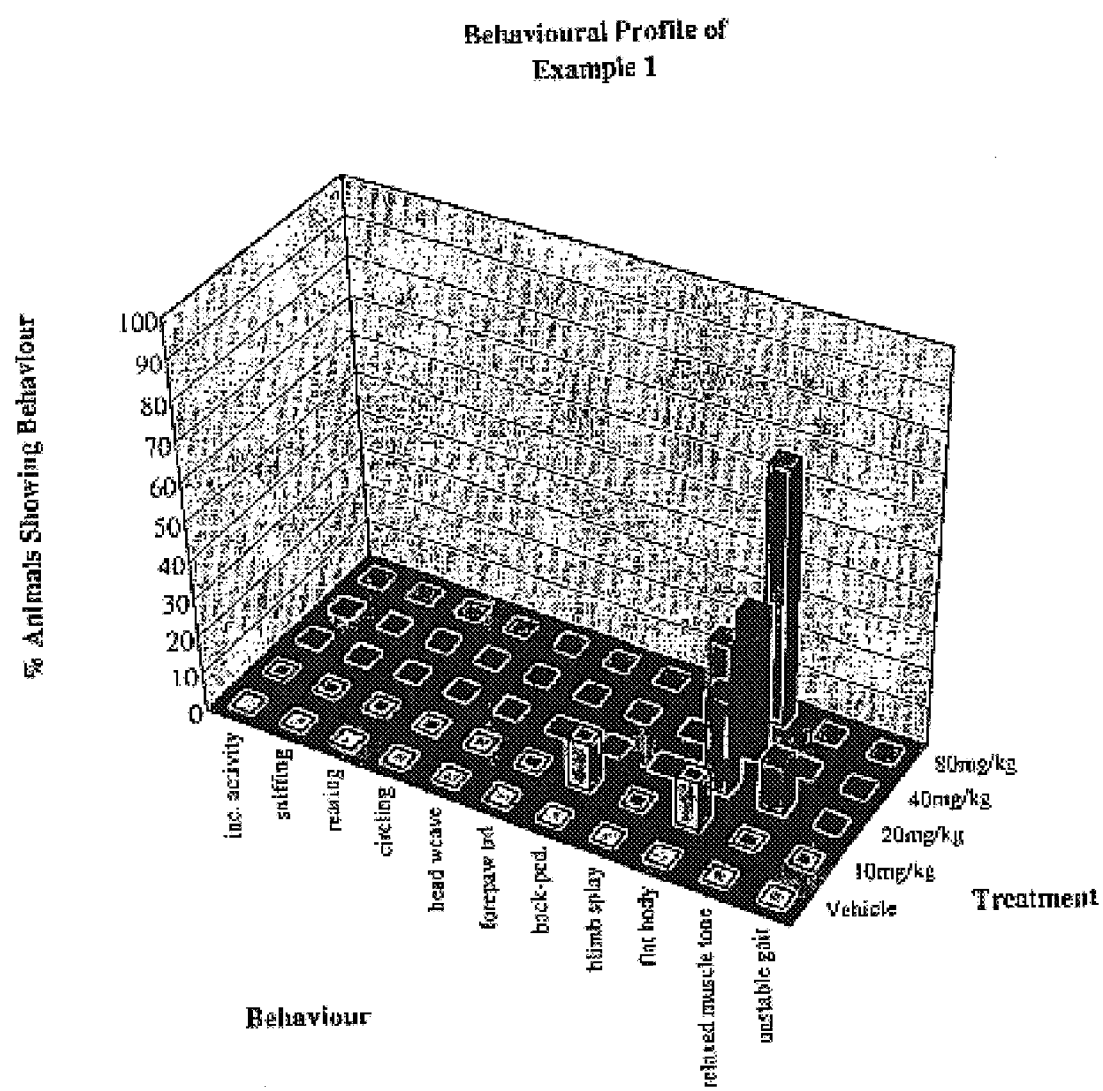
FIG. 2 shows the behavioral profile of Example 1. The compound of Example 1 was administered intraperitoneally at doses of 5, 10, 20 and 40 mg/kg twenty minutes prior to testing, and the percentage of animals in groups of n=8 animals showing PCP related behaviors was scored. Surprisingly, although the compound of Example 1 has similar in vitro binding potency to memantine, it shows no tendency to elicit "PCP syndrome."
Figure 3:
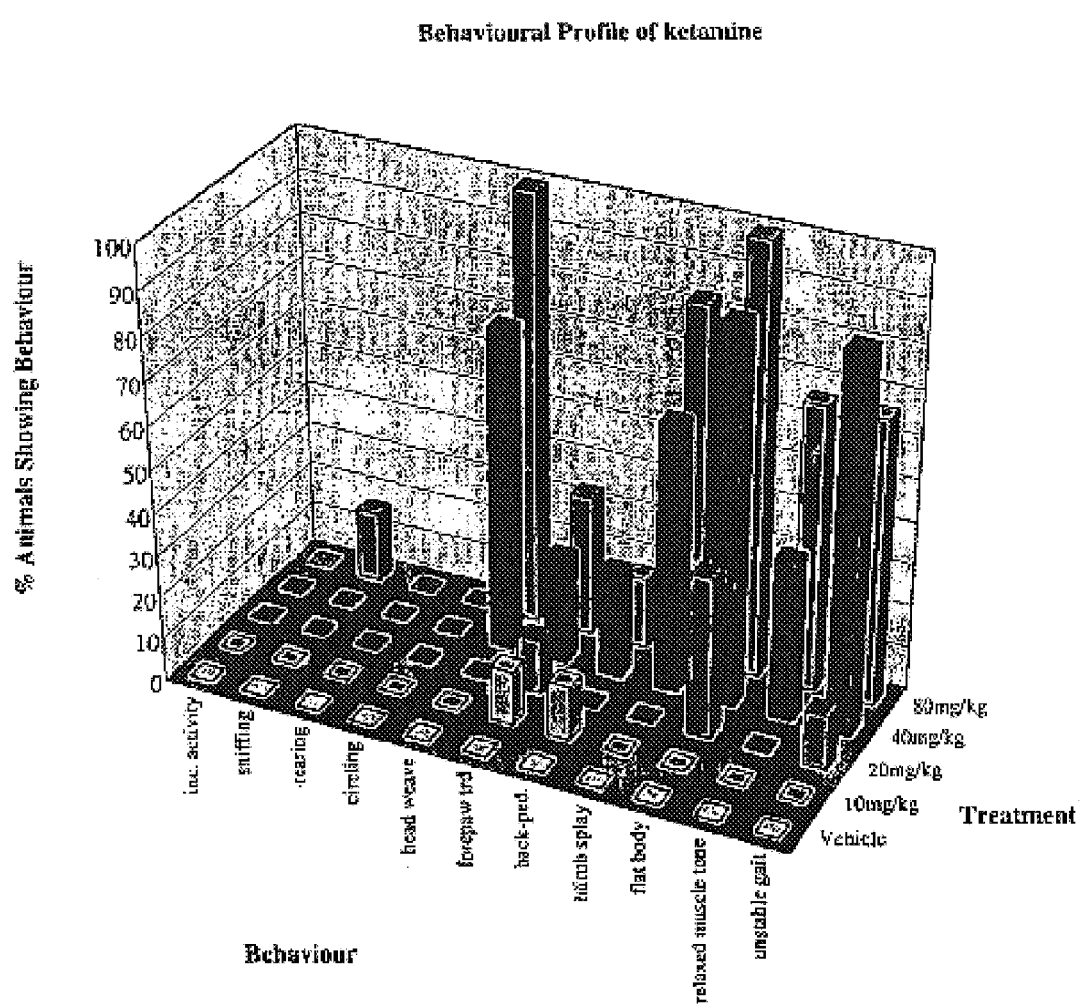
FIG. 3 shows the behavioral profile of ketamine. Ketamine was administered intraperitoneally at doses of 5, 10, 20 and 40 mg/kg twenty minutes prior to testing, and the percentage of animals in groups of n=8 animals showing PCP related behaviors was scored.

| Behaviour | Notation in FIGS. 1–3 |
| --- | --- |
| Increased locomotor activity | "inc activity" |
| Exploratory behaviour in the form of sniffing | "sniffing" |
| Exploratory behaviour in the form of rearing | "rearing" |
| Circling | "circling" |
| Side to side head weaving | "head weave" |
| Reciprocal forepaw treading | "forepaw trd" |
| Backwards locomotion | "back-ped." |
| Splayed hindlimb | "hlimb splay" |
| Flat body posture | "flat body" |
| Hypotonia (relaxed muscle tone) | "relaxed muscle tone" |
| Unstable gait | "unstable gait" |

Ratings were plotted on ethograms to illustrate the profile of effect of each test compound. Data for test compounds are presented in FIGS. 1–3.

FIG. 1 shows the behavioural profile of memantine. Memantine was administered intraperitoneally at doses of 5, 10, 20 and 40 mg/kg twenty minutes prior to test and the percentage of animals in groups of n=8 animals showing PCP related behaviours scored.

FIG. 2 shows the behavioural profile of Example 1. The compound of Example 1 was administered intraperitoneally at doses of 10, 20, 40 and 80 mg/kg 20 min prior to test and the percentage of animals in groups of n=8 animals showing PCP related behaviours scored.

FIG. 3 shows the behavioural profile of ketamine. Ketamine was administered intraperitoneally at doses of 10, 20, 40 and 80 mg/kg twenty minutes prior to test and the percentage of animals in groups of n=8 animals showing PCP related behaviours scored.

The data in FIG. 2 show that surprisingly, despite having similar in vitro binding potency to memantine, the compound of Example 1 shows no tendency to elicit "PCP syndrome" (see FIG. 2).

Figure 4:
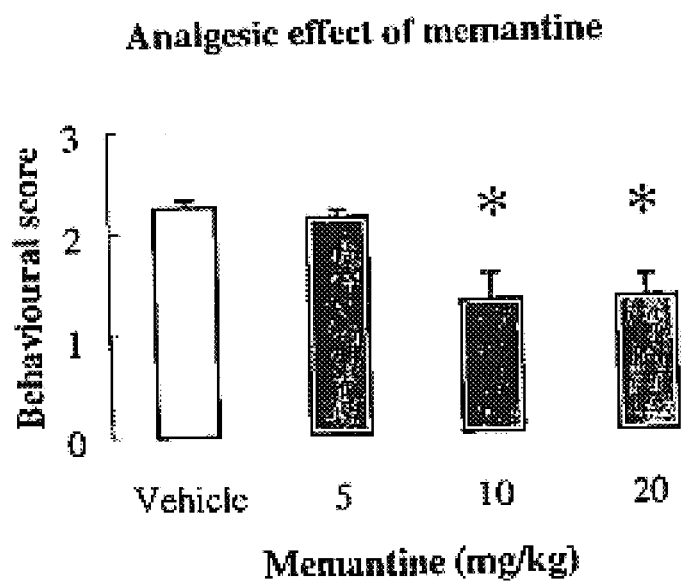
FIG. 4 shows the effect of memantine (5, 10 and 20 mg/kg) on the nociception related behaviors associated with sub-plantar injection of formalin into the rat hind paw. Memantine was effective over a dose range of 10 to 20 mg/kg, with a minimum effective dose of 10 mg/kg.
Figure 5:
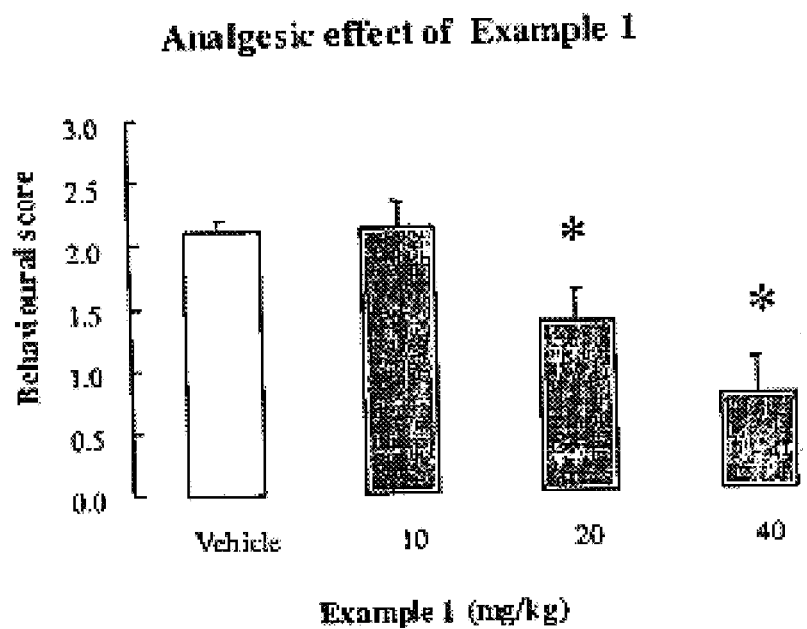
FIG. 5 shows the effect of Example 1(10, 20 and 40 mg/kg) on the nociception related behaviors associated with sub-plantar injection of formalin into the rat hind paw. Example 1 was effective over a dose range of 20 to 40 mg/kg, with a minimum effective dose of 20 mg/kg.
Figure 6:
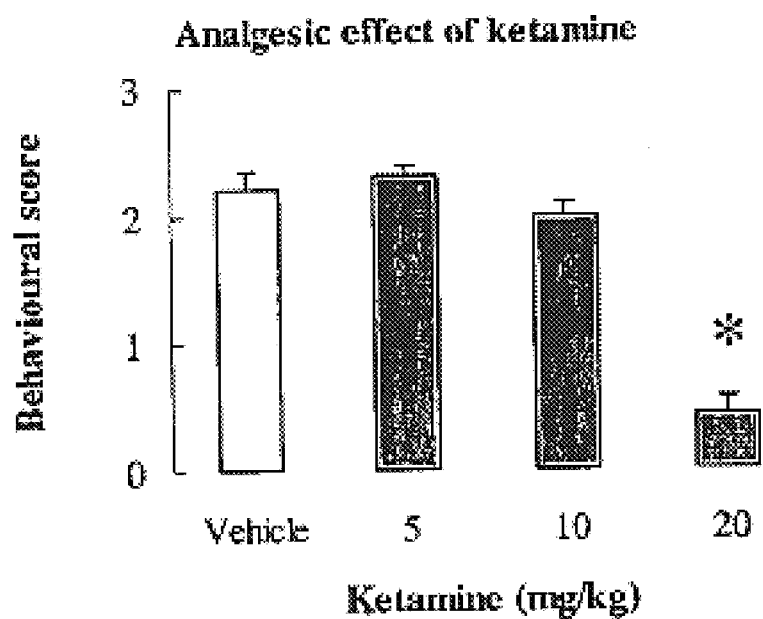
FIG. 6 shows the effect of ketamine (5, 10 and 20 mg/kg) on the nociception related behaviors associated with sub-plantar injection of formalin into the rat hind paw. Ketamine showed a minimum effective dose of 20 mg/kg.

Comparisons of side effect liability were made using these behavioural ratings after the administration of doses of compound that were equally effective as analgesics (see FIGS. 4 to 6).

IV. Assessment of Analgesia

Analgesia testing was performed in male Sprague Dawley rats weighing 200–250 g. Drugs were administered 20 minutes prior to a sub-plantar injection of formalin into the right hind paw. The characteristic nociceptive behavioural responses elicited by this injection were rated on a scale from "0"=no effect through to "3"=effect of maximal intensity. As with side effect ratings, all observations were made blind to treatment condition. Ratings of nociception related behaviours were made in two time periods, one from the time of injection for a further five minutes (t=0 to t=5 min), and a second from t=5 min to t=30 min. The response to formalin injection in this model is biphasic, the first phase occurring during the first five minutes consists of a primary inflammation related response. The second phase, occurring over the subsequent 30 minutes is a delayed phase in which the phenomenon of "wind up" or neurally mediated hyperalgesia, is thought to occur. It is the second phase of response that has relevance to sciatica, diabetic neuropathy and other neuropathic chronic pain states. Responses to test compounds were assessed during this second phase from t=5 min to t=30 min. Data were analysed by means of Median tests followed by post hoc Bonferroni corrected Mann-Whitney U-tests. Data for test compounds are presented in FIGS. 4–6.

FIG. 4 shows the effect of memantine (5, 10 and 20 mg/kg) on the nociception related behaviours associated with sub-plantar injection of formalin into the rat hind paw. Memantine was effective over a dose range of 10 to 20 mg/kg, with a minimum effective dose of 10 mg/kg.

FIG. 5 shows the effect of Example 1 (10, 20 and 40 mg/kg) on the nociception related behaviours associated with sub-plantar injection of formalin into the rat hind paw. Example 1 was effective over a dose range of 20 to 40 mg/kg, with a minimum effective dose of 20 mg/kg.

FIG. 6 shows the effect of ketamine (5, 10 and 20 mg/kg) on the nociception related behaviours associated with sub-plantar injection of formalin into the rat hind paw. Ketamine showed a minimum effective dose of 20 mg/kg.

What is claimed is:

1. A method of treatment of a condition generally associated with abnormalities in glutamatergic transmission, comprising administering, to a patient in need of such treatment, a pharmaceutically effective dose of a compound of formula (1):

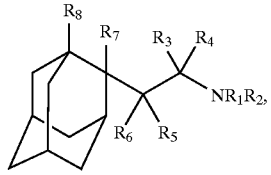

(1)

wherein $R_1$, $R_2$, $R_3$, $R_4$, $R_5$ and $R_6$ are independently selected from hydrogen, alkyl, aryl and non-aromatic heterocyclic groups, or each of one or more pair(s) of the substituent groups $R_1$ to $R_6$ may together form a 3, 4, 5, 6, 7 or 8-membered ring containing 0, 1 or 2 heteroatom(s);

$R_7$ is selected from alkyl, aryl and non-aromatic heterocyclic groups; and $R_8$ is selected from hydrogen, halogen, alkyl, aryl and non-aromatic heterocyclic groups;

or a pharmaceutically acceptable salt or prodrug thereof.

2. The method according to claim 1 wherein $R_8$ is selected from hydrogen, alkyl, aryl and non-aromatic heterocyclic groups.

3. The method according to claim 1 wherein $R_1$, $R_2$, $R_3$, $R_4$, $R_5$ and $R_6$ are independently selected from hydrogen, alkyl and aryl, or each of one or more pair(s) of the substituent groups $R_1$ to $R_6$ may together form a 3, 4, 5, 6, 7 or 8-membered ring containing 0, 1 or 2 heteroatom(s); $R_7$ is selected from alkyl and aryl; and $R_8$ is selected from hydrogen, halogen, alkyl and aryl.

4. The method according to claim 3 wherein $R_8$ is selected from hydrogen, alkyl and aryl.

5. The method according to claim 1 wherein $R_1$ to $R_6$ and $R_8$ are independently selected from hydrogen and alkyl.

6. The method according to claim 1 wherein $R_1$ to $R_6$ and $R_8$ are independently selected from lower alkyl.

7. The method according to claim 1 wherein $R_1$ to $R_6$ and $R_8$ are independently selected from acyclic lower alkyl.

8. The method according to claim 1 wherein one or both of $R_1$ and $R_2$ is selected from hydrogen and methyl.

9. The method according to claim 1 wherein one or both of $R_3$ and $R_4$ is selected from hydrogen and methyl.

10. The method according to claim 1 wherein one or both of $R_5$ and $R_6$ is selected from hydrogen and methyl.

11. The method according to claim 1 wherein a ring formed by a pair of the substituent groups $R_1$ to $R_6$ contains 0 or 1 heteroatom(s).

12. The method according to claim 1 wherein a ring formed by a pair of the substituent groups $R_1$ to $R_6$ is saturated or partially unsaturated.

13. The method according to claim 1 wherein a ring formed by a pair of the substituent groups $R_1$ to $R_6$ is saturated.

14. The method according to claim 1 wherein $R_7$ is selected from cycloalkyl, unsubstituted acyclic alkyl, acyclic alkyl substituted by a non-aromatic heterocyclic group, aryl-substituted acyclic alkyl, aryl and non-aromatic heterocyclic groups.

15. The method according to claim 1 wherein $R_7$ is selected from unsubstituted acyclic alkyl, aryl-substituted acyclic alkyl and aryl.

16. The method according to claim 1 wherein $R_7$ is selected from carbocyclic aromatic group.

17. The method according to claim 1 where $R_7$ is selected from 5 and 6-membered non-aromatic heterocyclic groups.

18. The method according to claim 1 wherein $R_7$ is selected from non-aromatic heterocyclic groups containing 1 or 2 heteroatoms selected from N, O and S.

19. The method according to claim 1 wherein $R_7$ is tolyl, phenyl, methoxyphenyl or thienyl.

20. The method according to claim 1 wherein $R_8$ is hydrogen.

21. The method according to claim 1 wherein the compound is selected from the group consisting of: 2-[2-(2-phenyl)adamantyl]ethylamine, 2-[2-[2-(2-thienyl)]adamantyl]ethylamine, 4-[2-[2-[2-(2-thienyl)]adamantyl]]ethylmorpholine, 1-[2-[2-[2-(2-thienyl)]adamantyl]]ethylpyrrolidine, 1-[2-[2-[2-(2-thienyl)]adamantyl]]ethylpiperidine, N-(2-methylpropyl)-2-[2-[2-(2-thienyl)]adamantyl]ethylamine, N-(4-methylbenzyl)-2-[2-[2-(2- thienyl)]adamantyl]ethylamine, 2-[2-[2-(4-methyl)phenyl]adamantyl]ethylamine, N-methyl-2-[2-[2-(4-methylphenyl)]adamantyl]ethylamine, N,N-dimethyl-2-[2-[2-(4-methylphenyl)]adamantyl]ethylamine, 2-[2-(2-methyl)adamantyl]ethylamine, 2-[2-(2-benzyl)adamantyl]ethylamine, 2-[2-(2-(3-methoxyphenyl))adamantyl]ethylamine, and 1-[2-[2-(4-methylphenyl)]adamantyl]-2-propylamine.

22. The method according to claim 1 wherein the compound is 2-[2-(2-phenyl)adamantyl]ethylamine.

23. The method or method according to claim 1 wherein said condition generally associated with abnormalities in glutamatergic transmission is a condition treatable by blockade of the N-methyl-D-aspartate (NMDA) receptor.

24. The method of claim 1 wherein said condition generally associated with abnormalities in glutamatergic transmission is a condition in which administration of an NMDA receptor antagonist would be beneficial.

25. The method of claim 1 wherein said condition generally associated with abnormalities in glutamatergic transmission is a condition selected from ischaemic stroke, haemorrhagic stroke, subarrachnoid haemorrhage, subdural haematoma, coronary artery bypass surgery, neurosurgery, traumatic brain injury, traumatic spinal injury, Alzheimer's disease, Parkinson's disease, Huntington's disease, Pick's disease, Lewy body disease, senile dementia, spongiform encephalopathies, prion-protein induced neurotoxicity, perinatal asphyxia, demyelinating disease, multiinfarct dementia, vascular dementia, dementia puglians, drug dependence, alcohol withdrawal, opiate withdrawal, motor neurone disease, multiple sclerosis, acute and chronic pain, cancer pain, trigeminal neuralgia, migraine, pain caused by excessive vasodilation, cluster headache, primary and secondary hyperalgesia, inflammatory pain, nociceptive pain, tabes dorsalis, phantom limb pain, spinal cord injury pain, central pain, post herpetic pain, HIV pain and diabetic neuropathy.

26. The method of claim 1 wherein said condition generally associated with abnormalities in glutamatergic transmission is a condition selected from epilepsy, AIDS dementia, multiple system atrophy, progressive supranuclear palsy, Friedrich's ataxia, autism, fragile X syndrome, tuberous sclerosis, attention deficit disorder, olivio-ponto-cerebellar atrophy, cerebral palsy, drug-induced optic neuritis, peripheral neuropathy, myelopathy, ischaemic retinopathy, glaucoma, cardiac arrest, meningitis, encephalitis, depression, bi-polar disorder, schizophrenia, psychosis, behavior disorders, impulse control disorders, pre-eclampsia, neuroleptic malignant syndrome, chronic fatigue syndrome, anorexia nervosa, anxiety disorders, generalized anxiety disorder, panic disorder, phobias, fresh water drowning and decompression.

27. The method of claim 1 wherein said condition is neuropathic pain or vasodilatory headache.

28. The method of claim 1 wherein said treatment is the reduction or prevention of the progression of said condition.

29. The method of claim 28 wherein said condition is a neurodegenerative disorder.

30. A compound of formula (1):

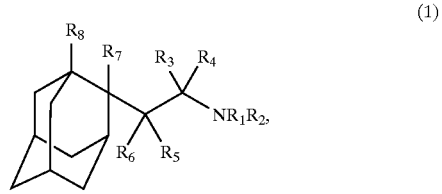

wherein $R_1, R_2, R_3, R_4, R_5$ and $R_6$ are independently selected from hydrogen, alkyl, aryl and non-aromatic heterocyclic groups, or each of one or more pair(s) of the substituent groups $R_1$ to $R_6$ may together form a 3, 4, 5, 6, 7 or 8-membered ring containing 0, 1 or 2 heteroatom(s);

$R_7$ is selected from alkyl, aryl and non-aromatic heterocyclic groups; and $R_8$ is selected from hydrogen, halogen, alkyl, aryl and non-aromatic heterocyclic groups;

and pharmaceutically acceptable salts and prodrugs thereof, other than compounds wherein $R_7$ is 3-aminopropyl.

31. The compound as defined in claim 30 other than compounds wherein $R_7$ is an alkyl group substituted by a substituent other than one selected from aryl and non-aromatic heterocycles.

32. The compound as defined in claim 30 wherein $R_7$ is selected from cycloalkyl, unsubstituted acyclic alkyl, acyclic alkyl substituted by a non-aromatic heterocyclic group.

33. The compound as defined in claim 32, wherein $R_7$ is selected from unsubstituted acyclic alkyl, alkyl substituted by aryl, and aryl.

34. A pharmaceutical composition, comprising a compound according to claim 30 in combination with an pharmaceutically acceptable excipient.

* * * * *